(12) United States Patent
Ariyoshi et al.

(10) Patent No.: US 8,504,301 B2
(45) Date of Patent: Aug. 6, 2013

(54) SAMPLE ANALYZER, METHOD FOR DISPLAYING ANALYSIS RESULT INFORMATION OF A SAMPLE AND COMPUTER PROGRAM PRODUCT

(75) Inventors: Shunsuke Ariyoshi, Kobe (JP); Toru Mizumoto, Kobe (JP); Hiroo Tatsutani, Kobe (JP)

(73) Assignee: Sysmex Corporation, Kobe (JP)

( * ) Notice: Subject to any disclaimer, the term of this patent is extended or adjusted under 35 U.S.C. 154(b) by 560 days.

(21) Appl. No.: 12/459,896

(22) Filed: Jul. 8, 2009

(65) Prior Publication Data

US 2010/0010746 A1    Jan. 14, 2010

(30) Foreign Application Priority Data

Jul. 9, 2008 (JP) ................................. 2008-179036
Aug. 25, 2008 (JP) ................................. 2008-215728

(51) Int. Cl.
*G01N 33/48* (2006.01)
*G06F 11/30* (2006.01)

(52) U.S. Cl.
USPC .............. 702/19; 702/182; 702/188; 702/189

(58) Field of Classification Search
USPC ............................ 702/19, 121–123, 179–189
See application file for complete search history.

(56) References Cited

FOREIGN PATENT DOCUMENTS

| JP | 11-083726 | 3/1999 |
|----|-----------|--------|
| JP | 2003-190097 | * 7/2003 |

* cited by examiner

*Primary Examiner* — Phuong Huynh
(74) *Attorney, Agent, or Firm* — Brinks Hofer Gilson & Lione

(57) ABSTRACT

The present invention is to present a sample analyzer comprising: an analysis result information generator for generating analysis result information including an analysis result of a sample; a display; a display controller for controlling the display so as to display the analysis result information generated by the analysis result information generator; an input receiver for receiving an input of a comment to one of the analysis result information; a memory for storing the comment received by the input receiver; and a determiner for determining whether another analysis result information to be displayed on the display meets with a predetermined condition, wherein the display controller controls the display so as to display the another analysis result information and the comment stored in the memory, when the determiner has determined that the another analysis result information meets with the predetermined condition.

20 Claims, 22 Drawing Sheets

Fig. 6

| User ID | Password | User group | Name |
|---|---|---|---|
| 0001 | ×××× | Managing technologist | Taro Tokkyo |
| 0002 | ○○○○ | Chief technologist | Hanako Jitsuyo |
| 0003 | △△△△ | Technologist | Jiro Isyo |
| 0004 | □□□□ | Physician | Saburo Shohyo |
| ⋮ | ⋮ | ⋮ | ⋮ |

Fig. 9

| Item | Actual data | Reading authority setting | Comment |
|---|---|---|---|
| Patient ID | 0001 | Unrestricted | Note: this patient has low PLT; Technologist Yamada |
| Attending physician | ○○ | Managing technologist technologist | Immediate submission of result is desired. |
| Particle distribution diagram | (Bit map data) | Technologist | Staphylococcus? |
| ⋮ | ⋮ | ⋮ | ⋮ |

SAMPLE ANALYZER, METHOD FOR DISPLAYING ANALYSIS RESULT INFORMATION OF A SAMPLE AND COMPUTER PROGRAM PRODUCT

RELATED APPLICATIONS

This application claims priority under 35 U.S.C. §119 to Japanese Patent Application Nos. 2008-179036 filed on Jul. 9, 2008 and 2008-215728 filed on Aug. 25, 2008, the entire contents of which are hereby incorporated by reference.

FIELD OF THE INVENTION

The present invention relates to a sample analyzer, a method and a computer program product for displaying analysis result information including an analysis result of a sample obtained from a subject.

BACKGROUND

Sample analyzers are known that analyze a sample such as urine or blood collected from a subject (patient), and display the obtained analysis result.

For example, Japanese Laid-Open Patent Publication No. H11-83726 discloses an automated white blood cell classifying apparatus for sequentially photographing a blood sample housed in a cassette by an imaging section, automatically classifying the white blood cells in the sample, and outputting, to a screen, the image of the automatically classified white blood cells, automated classification result, image of the red blood cells, and counting result. In this automated white blood cell classifying apparatus, an operator performs a review based on the aforementioned output, and the operator-reviewed classification result data, specifically, the classification result of each blood cell type, as well as the operator comments are output.

When the analysis result is referenced by another operator, it is useful to display the comments, such as opinions or cautionary notes of the first operator together with the analysis result as in the automated white blood cell classifying apparatus disclosed in Japanese Laid-Open Patent Publication No. H11-83726 so that the other operator can comprehend the opinion or cautionary note. However, when a comment is associated to one analysis result, that comment cannot be displayed when viewing another analysis result to which a comment is not associated. That is, when several analysis results have something in common and a comment related to this commonality is associated with one analysis result, the comment cannot be displayed when another analysis result is displayed. It is also difficult to find the analysis result to which the desired comment is associated. It cannot be said, therefore, that the automated white blood cell classifying apparatus disclosed in Japanese Laid-Open Patent Publication No. H11-83726 is configured to make comments sufficiently usable.

SUMMARY OF THE INVENTION

The first aspect of the present invention is a sample analyzer comprising: an analysis result information generator for generating analysis result information including an analysis result of a sample; a display; a display controller for controlling the display so as to display the analysis result information generated by the analysis result information generator; an input receiver for receiving an input of a comment to one of the analysis result information; a memory for storing the comment received by the input receiver; and a determiner for determining whether another analysis result information to be displayed on the display meets with a predetermined condition, wherein the display controller controls the display so as to display the another analysis result information and the comment stored in the memory, when the determiner has determined that the another analysis result information meets with the predetermined condition.

The second aspect of the present invention is a sample analyzer comprising: a display; a memory; and a controller being configured to perform operations, comprising: generating an analysis result information including an analysis result of a sample; receiving an input of a comment to one of the analysis result information; storing the received comment in the memory; determining whether another analysis result information to be displayed on the display meets with a predetermined condition; and controlling the display so as to display the another analysis result information and the comment stored in the memory when the another analysis result information has been determined to meet with the predetermined condition.

The third aspect of the present invention is a method for displaying analysis result information of a sample, comprising steps of: (a) generating analysis result information including an analysis result of a sample; (b) receiving an input of a comment to one of the analysis result information; (c) storing the received comment in a memory; (d) determining whether another analysis result information of a display object meets with a predetermined condition; and (e) displaying the another analysis result information and the comment stored in the memory when it has been determined that the another analysis result information meets with the predetermined condition in the step (d).

The fourth aspect of the present invention is a computer program product, comprising: a computer readable medium, and software instructions, on the computer readable medium, for enabling a computer to perform predetermined operations comprising: (a) generating analysis result information including an analysis result of a sample; (b) receiving an input of a comment to one of the analysis result information; (c) storing the received comment in a memory; (d) determining whether another analysis result information to be displayed on a display device meets with a predetermined condition; and (e) displaying the another analysis result information and the comment stored in the memory on the display device, when it has been determined that the another analysis result information meets with the predetermined condition.

BRIEF DESCRIPTION OF THE DRAWINGS

FIG. 6 is a schematic view showing the structure of the user information database;

FIG. 9 is a schematic view showing the structure of the comment retrieval database;

DETAILED DESCRIPTION OF THE PREFERRED EMBODIMENTS

The preferred embodiments of the present invention are described hereinafter with reference to the drawings.

First Embodiment

The present embodiment is a sample analyzer which displays comments related to the analysis result among previously input comments, when analyzing tangible components in urine and displaying an analysis result screen that includes a scattergram.

[Structure of the Sample Analyzer]

Figure 1:
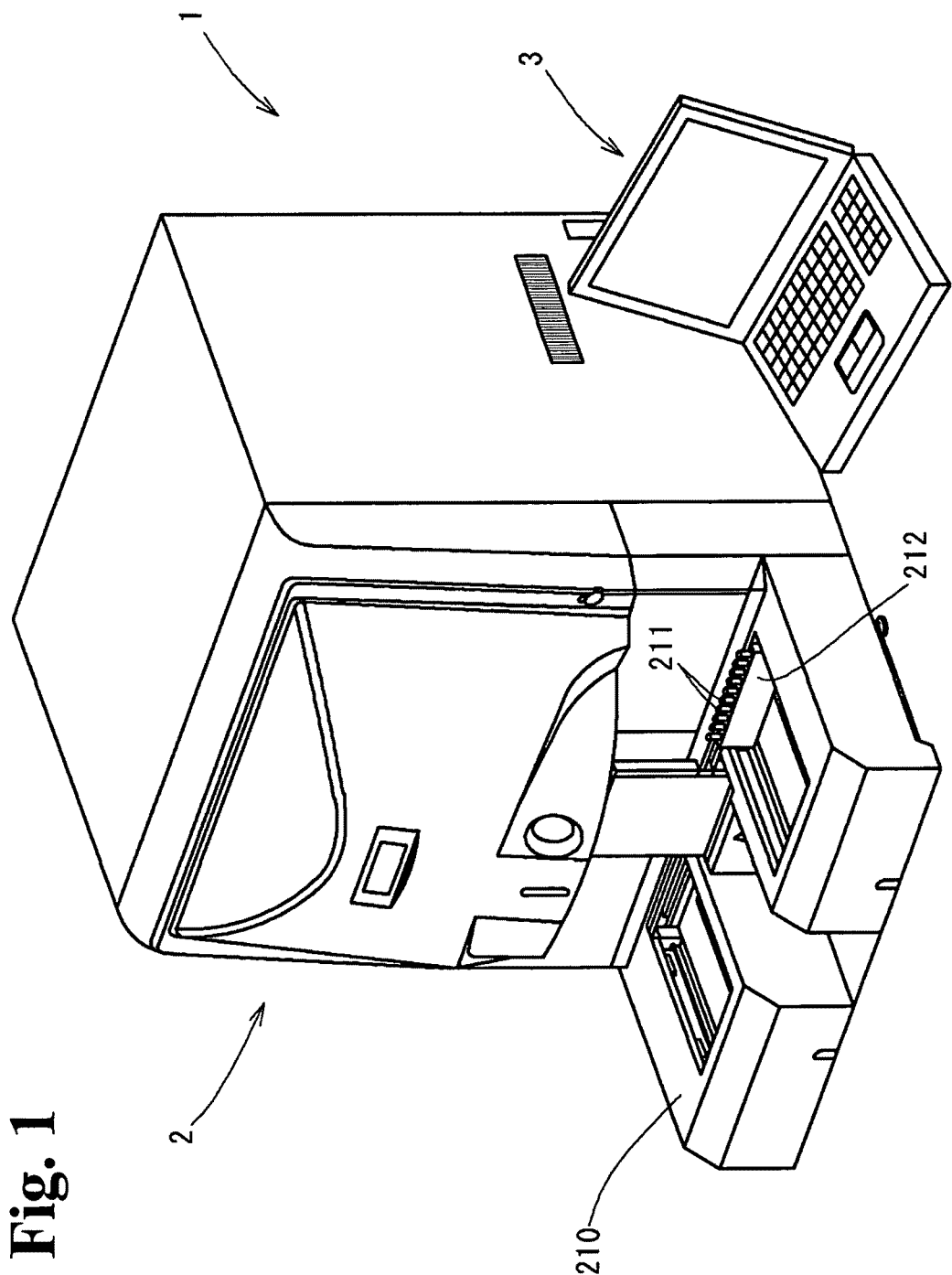
FIG. 1 is a perspective view briefly showing the structure of an embodiment of the sample analyzer.

FIG. 1 is a perspective view briefly showing the structure of an embodiment of the sample analyzer. As shown in FIG. 1, a sample analyzer 1 is configured by a measuring unit 2 for measuring a sample, and an information processing unit 3 for processing the measurement data output from the measuring unit 2 and displaying the sample analysis results. A transporting section 210 is provided on the front side of the measuring unit 2 so that a rack 212 which holds a plurality of test tubes 211 containing sample (urine) is transported by the transporting section 210.

<Structure of the Measuring Unit 2>

Figure 2:
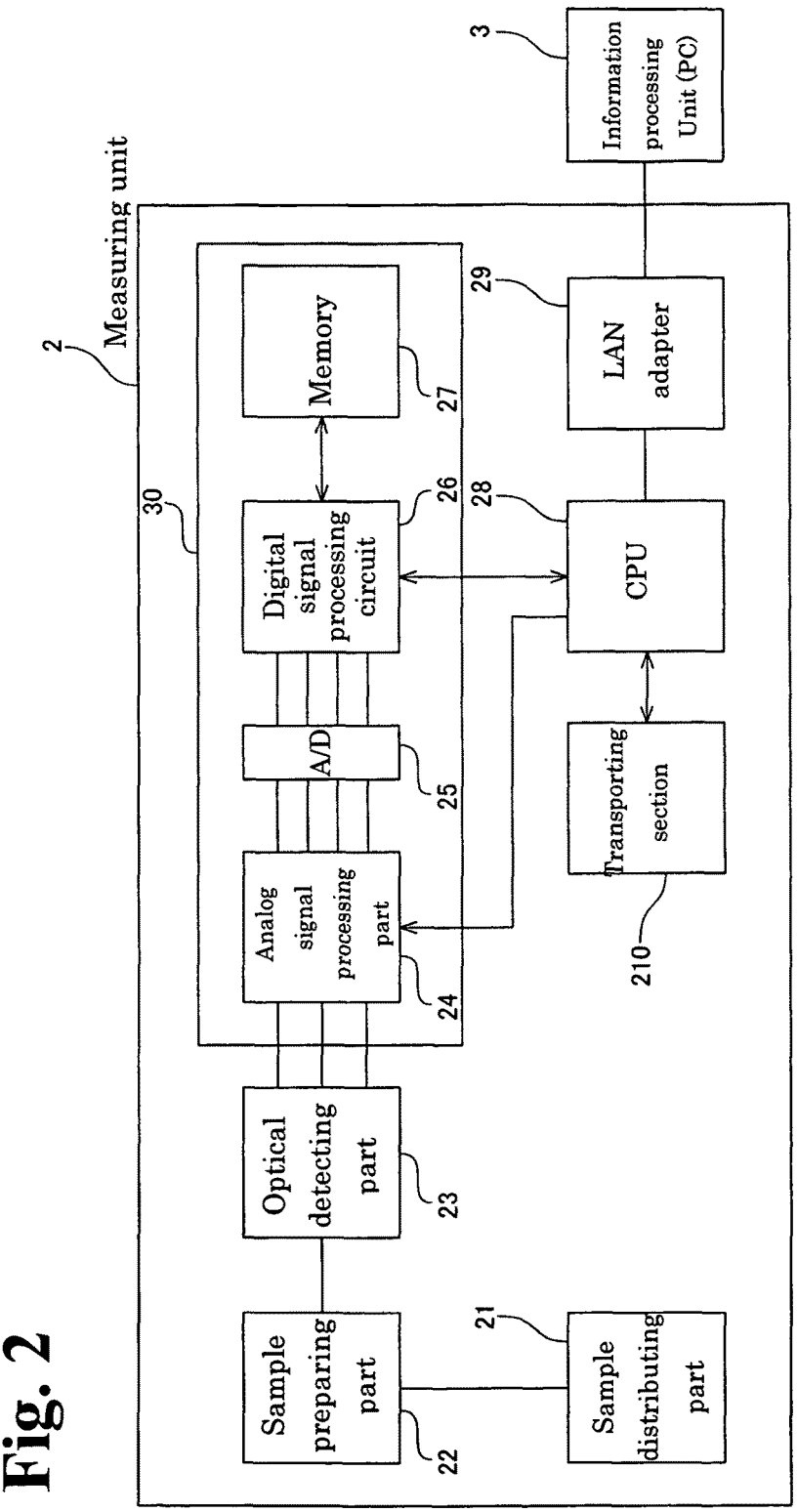
FIG. 2 is a block diagram showing the structure of the measuring unit.

FIG. 2 is a block diagram showing the structure of the measuring unit. As shown in FIG. 2, the measuring unit 2 is provided with a sample distributing part 21, sample preparing part 22, optical detecting part 23, analog signal processing circuit 24 for performing amplification and filter processing of the output from the optical detecting part 23, A/D converter 25 for converting the output of the analog signal processing circuit 24 to digital signals, digital signal processing circuit 26 for performing predetermined waveform processing of the digital signals, memory 27 which is connected to the digital signal processing circuit 26, CPU 28 which is connected to the analog signal processing circuit 24 and the digital signal processing circuit 26, LAN adapter 29 which is connected to the CPU 28, and the transporting section 210. The information processing unit 3 is connected to the measuring unit 2 through a LAN via the LAN adapter 29. Furthermore, the analog signal processing circuit 24, A/D converter 25, digital signal processing circuit 26, and memory 27 configure a signal processing circuit 30 for the electrical signals output from the optical detecting part 23.

The sample distributing part 21 is configured to dispense the urine sample in a predetermined distribution amount to the sample preparing part 22. The sample preparing part 22 is also configured to prepare a measurement sample using the reagent and urine dispensed by the sample distributing part 1, and supplies the prepared measurement sample together with a sheath fluid to a sheath flow cell 23c of the optical detecting part which will be described later.

Figure 3:
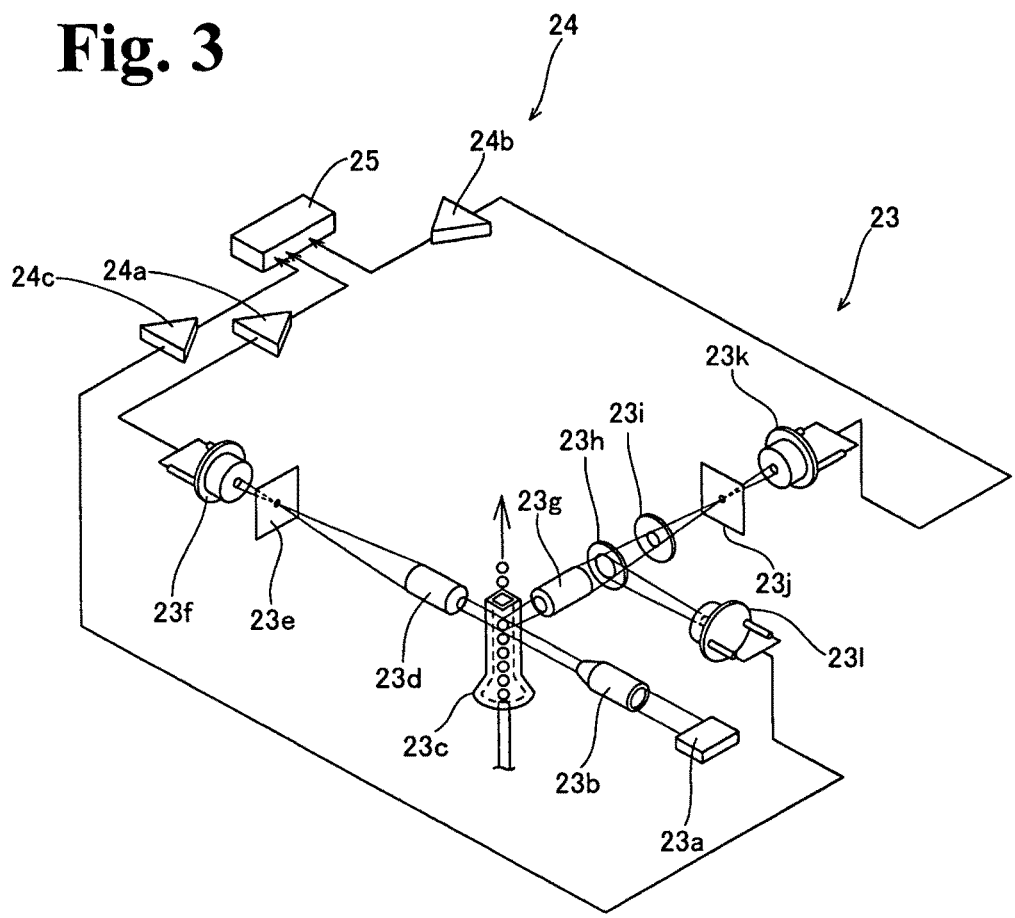
FIG. 3 is a schematic diagram showing the structure of the optical detecting section.

FIG. 3 is a schematic diagram showing the structure of the optical detecting part 23. As shown in FIG. 3, the optical detecting part 23 includes a light-emitting part 23a for emitting laser light, illumination lens unit 23b, sheath flow cell 23c to be illuminated by the laser light, collective lens 23d which is disposed on a line extending in the direction of travel of the laser light emitted from the light-emitting part 23a, pinhole 23e and PD (photodiode) 23f, collective lens 23g which is disposed in a direction intersecting the direction of travel of the laser light emitted from the light-emitting part 23a, dichroic mirror 23h, optical filter 23i, pinhole 23j and PD 23k, and APD (avalanche photodiode) 231 disposed on the dichroic mirror 23h side.

The light-emitting part 23a is provided to emit light toward a sample flow containing a measurement sample which passes within the sheath flow cell 23c. The illumination lens unit 23b is provided to render the light emitted from the light-emitting part 23a into parallel rays. The PD 23f is provided to receive the forward scattered light emitted from the sheath flow cell 23c.

The dichroic mirror 23h is provided to separate the side scattered light and the side fluorescent light emitted from the sheath flow cell 23c. Specifically, the dichroic mirror 23h is provided to direct the side scattered light emitted from the sheath flow cell 23c to the PD 23k, and direct the side fluorescent light emitted from the sheath flow cell 23c to the APD 231. The PD 23k is also provided to receive the side scattered light. The APD 231 is also provided to receive the side fluorescent light. The PD 23f, PD 23k, and APD 231 respectively have the function of converting the received optical signals to electrical signals.

The analog signal processing circuit 24 is provided with amps 24a, 24b, and 24c, as shown in FIG. 3. The amps 24a, 24b, and 24c are respectively provided to perform amplification and waveform processing on the electrical signals output from the PD23f, PD23k, and APD 231.

<Structure of the Information Processing Unit>

Figure 4:
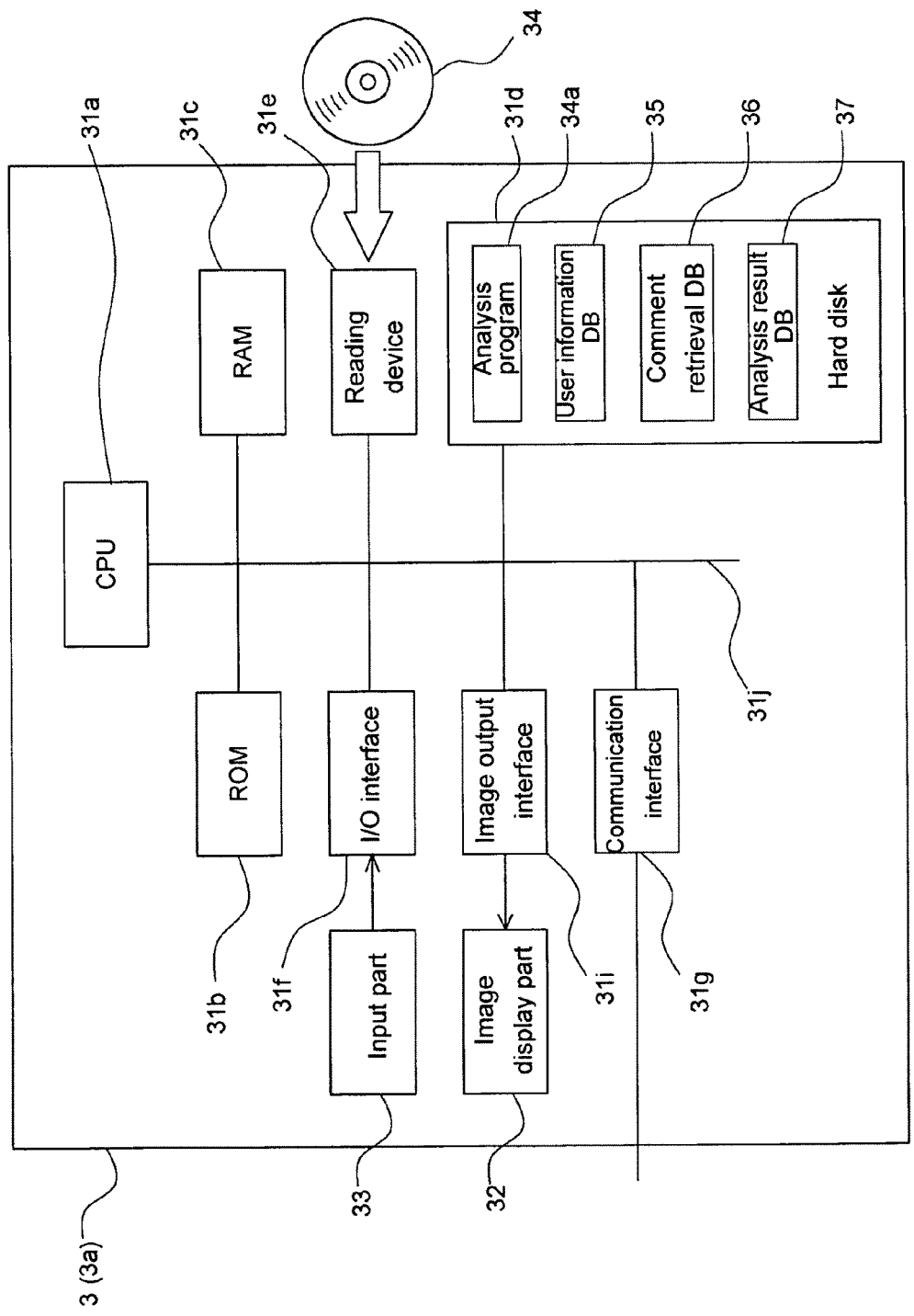
FIG. 4 is a block diagram showing the structure of the information processing unit.

FIG. 4 is a block diagram showing the structure of the information processing unit 3. The information processing unit 3 is realized by a computer 3a. As shown in FIG. 4, the computer 3a is provided with a CPU 31a, ROM 31b, RAM 31c, hard disk 31d, reading device 31e, input/output (I/O) interface 31f, communication interface 31g, image output interface 31i, image display part 32, and input part 33, and the CPU 31a, ROM 31b, RAM 31c, hard disk 31d, reading device 31e, input/output (I/O) interface 31f, communication interface 31g, image output interface 31i are connected by a bus 31j.

The CPU 31a is capable of executing computer programs loaded in the RAM 31c. The computer 3a functions as the information processing unit 3 when the CPU 31a executes an analysis program 34a which is described later.

The ROM 31b is configured by a mask ROM, PROM, EPROM, EEPROM or the like, and records the computer programs to be executed by the CPU 31a as well as the data used by those computer programs.

The RAM 31c is configured by SRAM, DRAM or the like. The RAM 31c is used when reading the analysis program 34a recorded on the hard disk 31d. The RAM 31c is also used as the work area of the CPU 31a when the CPU 31a executes computer programs.

The hard disk 31d stores an operating system, application programs and the like, and the various computer programs to be executed by the CPU 31a as well as the data used in the execution of the computer programs. Also installed on the hard disk 31d is the analysis program 34a which is described later.

The reading device 31e is configured by a floppy disk drive, CD-ROM drive, DVD-ROM drive or the like, and is capable of reading computer programs or data recorded on a portable recording medium 34. The portable recording medium 34 stores the analysis program 34a which enables the computer to function as the information processing unit, so that the computer 3a can read the analysis program 34a from the portable recording medium 34, and install the analysis program 34a on the hard disk 31d.

Note that the analysis program 34a cannot only be provided by the portable recording medium 34, the analysis program 34a may also be provided over an electrical communication line from an external device which is connected to the computer 3a via the electrical communication line (either wireless or wired) so as to be capable of communication. For example, the analysis program 34a may be stored on the hard disk of a server computer on the Internet so that the computer 3a can access the server computer, download the computer program, and install the computer program on the hard disk 31d.

A multitasking operating system such as Microsoft Windows (registered trademark of Microsoft Corporation, USA) may also be installed on the hard disk 31d. In the following description, the analysis program 34a of the present embodiment also operates on this operating system.

The I/O interface 31f may be a serial interface such as, for example, a USB, IEEE 1394, RS-232C or the like, a parallel interface such as a SCSI, IDE, IEEE 1284 or the like, and an analog interface configured by an D/A converter, A/D converter or the like. The input part 33 configured by a keyboard and mouse is connected to the I/O interface 31f so that a user may use the input part 33 to input data to the computer 3a.

The communication interface 31g is an Ethernet (registered trademark) interface. The communication interface 31g is connected to the measuring unit 2 through a LAN. The computer 3a can send and receive data to and from the measuring unit 2 which is connected to the LAN by using a predetermined communication protocol through the communication interface 31g.

The image output interface 31i is connected to the image display part 32 which is configured by an LCD, CRT or the like, and outputs image signals corresponding to the image data from the CPU 31a to the image display part 32. The image display part 32 displays images (screens) according to the input image signals.

[Operation of the Sample Analyzer]

The operation of the sample analyzer 1 of the present embodiment is described below with reference to FIGS. 5A through 5C.

Figure 5A:
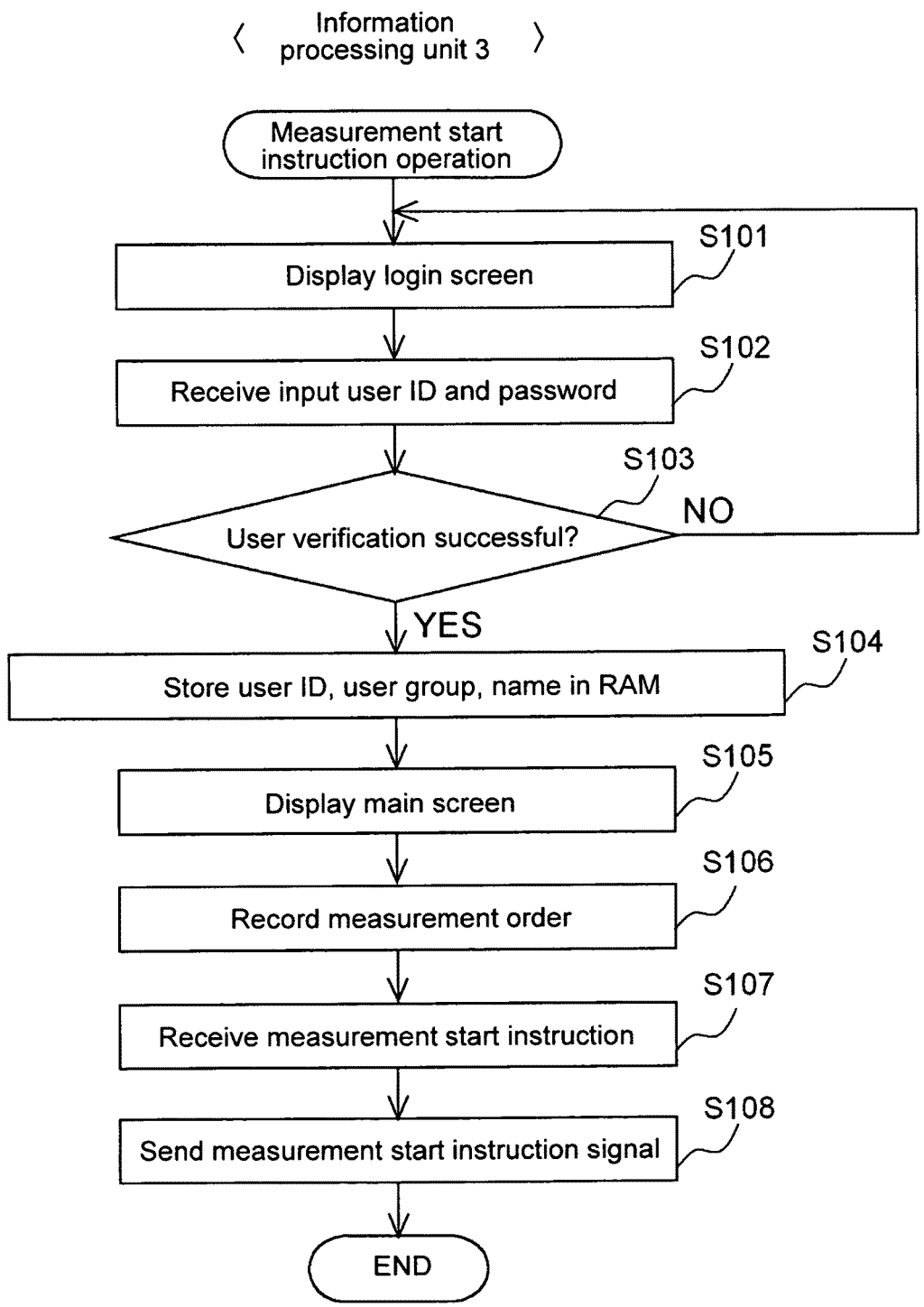
FIG. 5A is a flow chart showing the flow of the measurement start specification operation performed by the information processing unit.
Figure 5B:
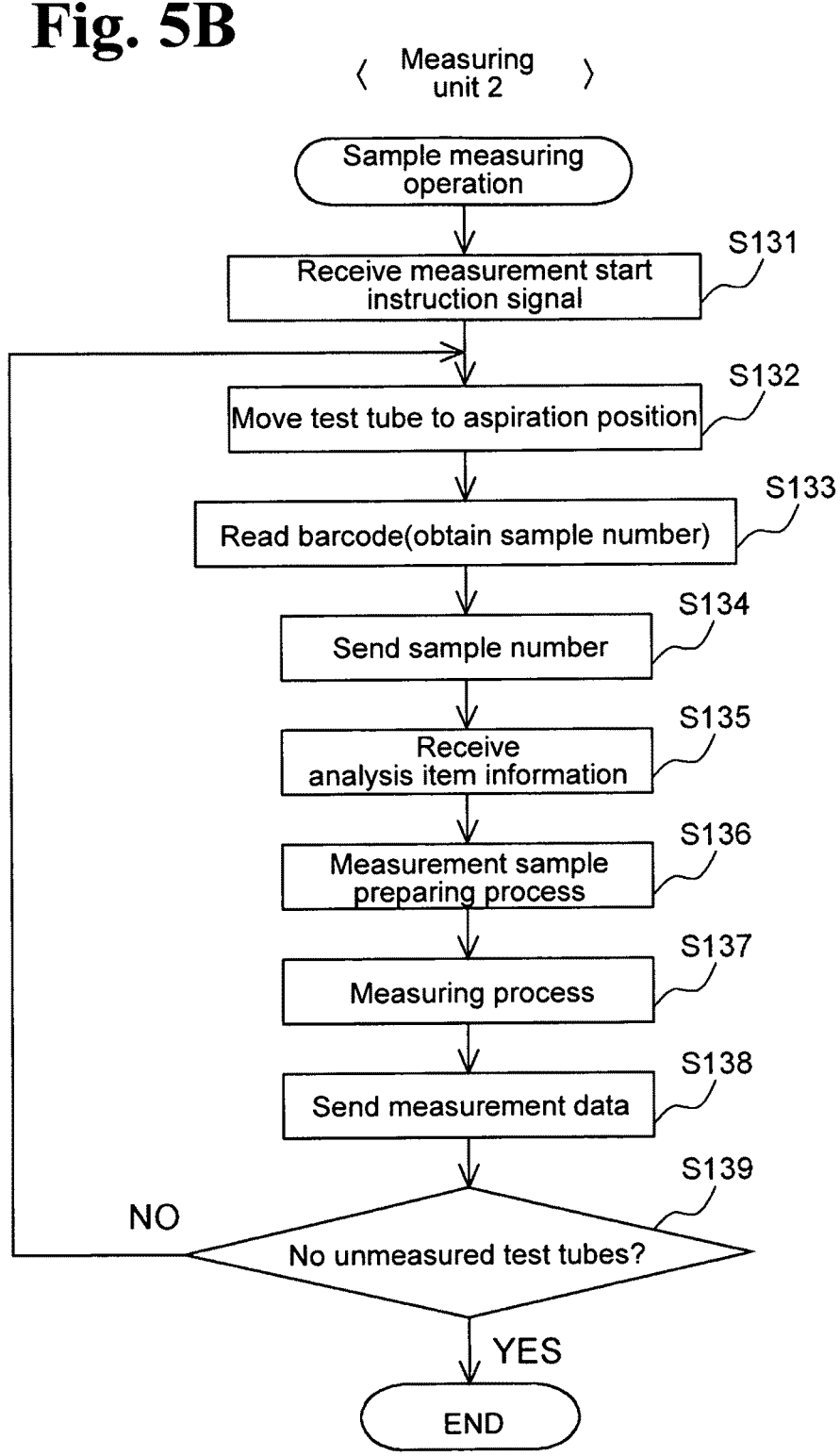
FIG. 5B is a flow chart showing the flow of the measurement operation performed by the measuring unit in the sample analysis operation of the sample analyzer.

When the user first starts the sample analyzer 1, initialization processes are executed for the measuring unit 2 and the information processing unit 3, whereupon the measuring unit 2 enters the measurement standby state and the CPU 31a of the information process unit 3 displays a login screen (not shown in the drawing on the image display part 32 (step S101 of FIG. 5A). In this state, when the user ID and password are input in the input area provided on the login screen and an operation is performed to enter the login instruction, the CPU 31a receives the login instruction together with the user ID and password. When the CPU 31a receives the login instruction data together with the user ID and password (step S102 of FIG. 5A), the CPU 31a generates an interrupt request and calls the process of step S103.

In step S103, the CPU 31a performs a user identification process. The user identification process is described in detail below. A user information database is provided on the hard disk 31d. FIG. 6 is a schematic view showing the structure of the user information database. The user information database 35 is a relational database provided with fields for a user ID 35a, password 35b, user group 35c, and user name 35d. Each record corresponds to a single each, and new records including the various input information can be added to the user information database 35 to record new data by inputting a user ID, password, and name in a user record screen which is not shown in the drawing.

The user ID is information specifically determined for each user and is used to identify the user. The password is set by the user and is used for user authentication. The user group include [chief technologist], [managing technologist], [technologist], [nurse], [serviceman], [administrator], and [physician], and each user must belong to at least one group. A comment reading authority which will be described later is determined for each user group. The name of each user is recorded in the user name field 35d. In the user authentication process, a determination is made as to whether the input user ID and password match a user ID and password recorded in the user information database 35. When the user authentication is successful (step S103: YES), the CPU 31a reads the user ID, user group, and user name of the user from the user information database 35 and stores the data in the RAM 31c (step S104), then displays the data on the main screen (not shown in the drawing) on the image display part 32 (step S105). On the other hand, when the user authentication fails (step S103: NO), the CPU 31a returns the process to step S101 and again displays the login screen.

The CPU 31a then executes a measurement data recording process (step S106). In the measurement data recording process, a measurement order including information of the analysis items and patient information such as a patient number (patient ID) of the patient from whim the sample was collected, name, age, sex, department, physician and the like, and specimen (sample) number (sample ID), are input to the information processing unit 3 manually by the user or by a host computer (not shown in the drawing) connected over the network, and the measurement order is then stored on the hard disk 31d by the CPU 31a.

When the user performed the start instruction operation by clicking a start button displayed on another screen than the main screen, the CPU 31a receives the measurement start instruction (step S107), the CPU 31a then generates an interrupt request and calls the process of step S108).

In step S108, the CPU 31a generates a measurement start instruction signal and sends the signal to the measuring unit 2 (step S108). Thereafter, the CPU 31a ends the process related to this measurement start instruction operation. The measurement operation of the measuring unit 2 shown in FIG. 5B is started by the measurement start instruction. When the measuring unit 2 receives the measurement start instruction signal (step S131 of FIG. 5B), an interrupt request is generated for the CPU 28 of the measuring unit 2, whereupon the CPU 28 controls the transport section 210 to move the sample rack 212 in which the sample-filled test tubes 211 are placed to a predetermined aspiration position (step S132). At the aspiration position, the test tube 211 is rotated, and the barcode of an ID label adhered to the outside of the test tube 11 is read by a barcode reader which is not shown in the drawing, and the read sample number is obtained by the CPU 28 (step S133). The CPU 28 sends the obtained sample number to the information processing unit 3 (step S134).

Figure 5C:
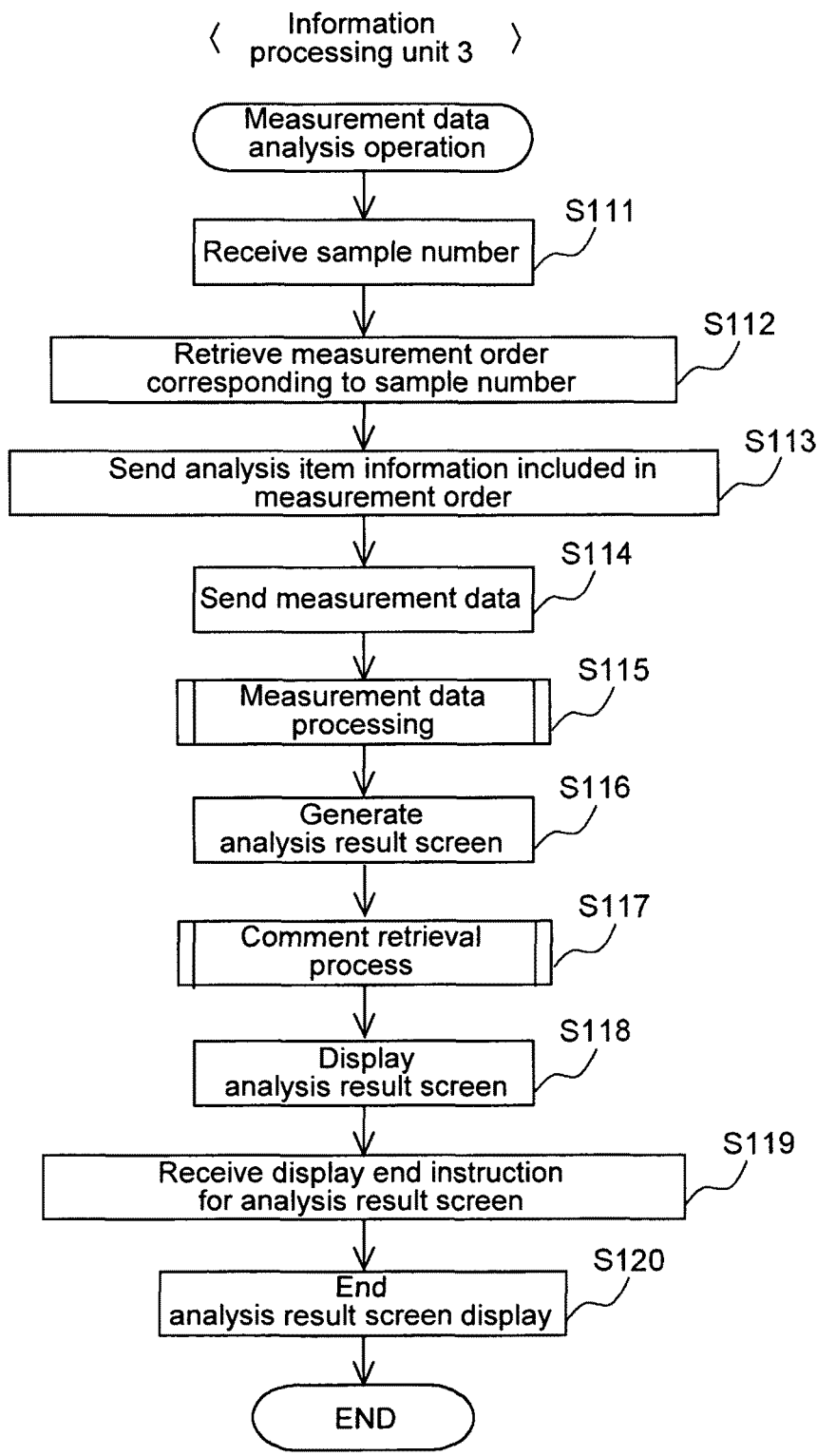
FIG. 5C is a flow chart showing the flow of the measurement data analysis operation performed by the information processing unit in the sample analysis operation of the sample analyzer.

The operation of the information processing unit 3 shown in FIG. 5C starts by the notification of the sample number. When the sample number is received by the information processing unit 3 (step S111 of FIG. 5), an interrupt request is generated by the CPU 31a and the CPU 31a retrieves the measurement order corresponding to the sample number from the hard disk 31d (step S112). The CPU 31a then sends the analysis item information contained in the retrieved measurement order to the measuring unit 2 (step S113).

When the measuring unit 2 receives the analysis item information (step S135 of FIG. 5B), an interrupt request is generated for the CPU 28 of the measuring unit 2 and the CPU 28 of the measuring unit 2 executes the measurement sample preparation process (step S136). In the measurement sample preparation process, the CPU 28 controls the sample distributing part 21 and sample preparing part 22 to prepare a measurement sample with urine and reagent. The prepared measurement sample is determined according to the measurement items. When measuring all measurement items, two types of measurement sample are prepared, including a first measurement sample for measuring urine sediment components (red blood cells, white blood cells, epithelial cells, casts and the like), and a second measurement sample for bacterial measurement.

The CPU 28 also executes the measurement process (step S137). In the measurement process, the CPU 28 controls the optical detecting part 23 to execute the optical measurements of the measurement sample. In the measurement process, measurements are performed according to the measurement items received from the information processing unit 3; when all measurement items are to be measured, a first measurement process which is a process to measure the first measurement sample, and a second measurement process which is a process to measure the second measurement sample, are executed. Specifically, in the measurement process, a sheath fluid is supplied to the sheath flow cell of the optical detecting part 23, and thereafter the first measurement sample to be used to measure urine sediment components (SED) is directed to the optical detecting part 23 and a thin flow (sheath flow) of the measurement sample encapsulated in the sheath fluid is formed in the sheath flow cell 23c. A laser beam emitted from the light-emitting part 23a then irradiates the sheath flow formed in this manner. The forward scattered light, fluorescent light, and side scattered light from the tangible components in the urine produced by the laser beam irradiation are respectively received by the photodiodes 23f, 23k, and APD 231 and converted to electrical signals which are then output as a forward scattered light signal (FSC), fluorescent light signal (FL), and side scattered light signal (SSC). These outputs are amplified by preamps. Thus, the first measurement process is performed first. On the other hand, when the first measurement process ends, the bacteria in the urine are then measured using the second measurement sample (second measurement process). In this case, the forward scattered light signal FSC) and fluorescent light signal (FL) are output and amplified similar to the case of the first measurement process by the optical detecting part 23 used for the measurement of tangible components in the urine. The amplified forward scattered light signal (FSC), fluorescent light signal (FL), and side scattered light signal (SSC) are converted to digital signals by the digital signal processing circuit 26, and thereafter subjected to predetermined waveform processing. Thus, measurement data are obtained which include forward scattered light data, side scattered light data, and side fluorescent light data of the first measurement sample, and forward scattered light data, side scattered light data, and side fluorescent light data of the second measurement sample. Then, the CPU 28 sends the obtained measurement data to the information processing unit 3 (step S138).

The CPU 28 also determines whether or not there is a remaining test tube which contains unmeasured sample (step S139). In this process, whether or not a test tube containing unmeasured sample is present in the sample rack disposed at the aspiration position is determined by providing a sensor on the transporting section 210. When the measurement of all test tubes in the sample rack is completed and the sample rack has been moved from the aspiration position, a determination is made as to whether or not there is a sample rack present which holds test tubes containing unmeasured sample. When a test tube containing unmeasured sample is present (step S139: NO), the process returns to step S132, the test tube containing the unmeasured sample is moved to the aspiration position, and the processes of step S133 and subsequent steps are repeated. On the other hand, when no test tube containing unmeasured sample remains (step S139: YES), the CPU 28 ends the process in step S139.

Figure 7:
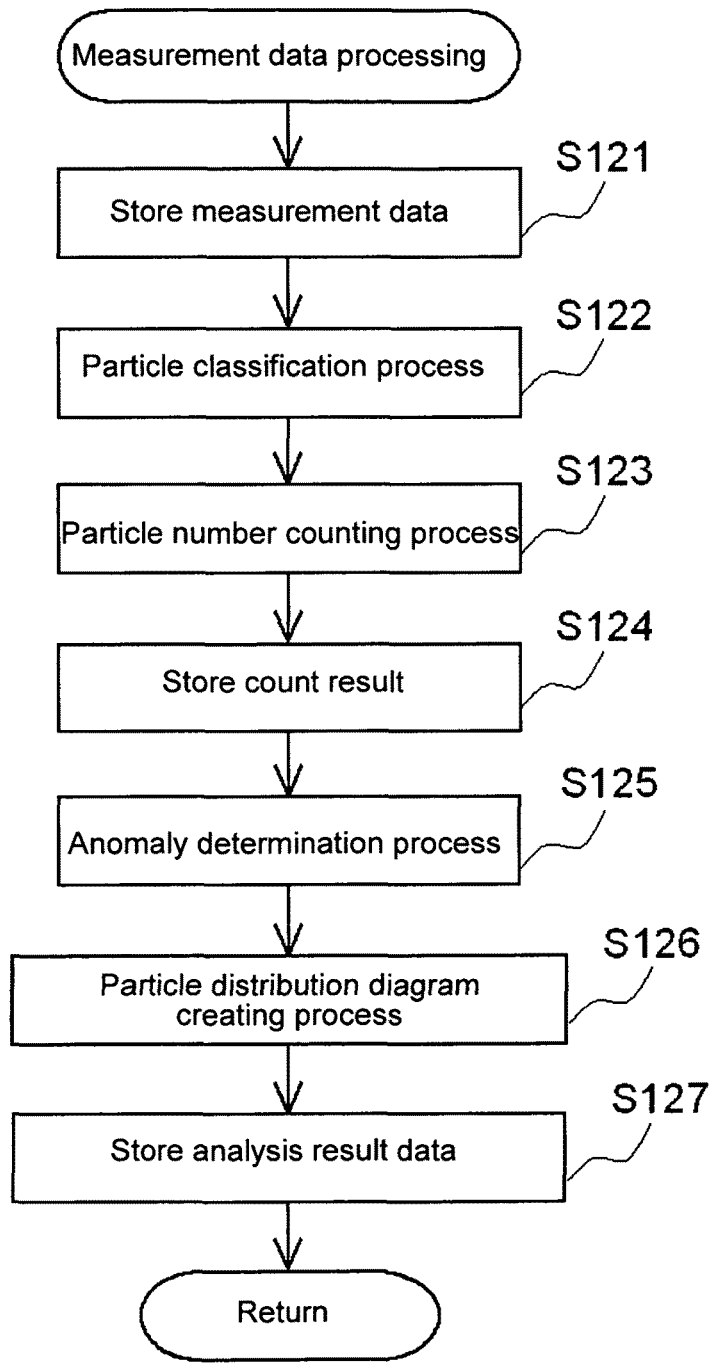
FIG. 7 is a flow chart showing the sequence of the processing of the measurement data performed by the information processing unit.

When the measurement data are received by the information processing unit 3 (step S114 of FIG. 5C), an interrupt request is generated for the CPU 31a, and the CPU 31a executes the measurement data processing (step S115). FIG. 7 is a flow chart showing the sequence of the processing of the measurement data performed by the information processing unit 3. In this measurement data processing, a scattergram and histogram are created which show the distribution state of the particles present in the sample as described below.

In the measurement data processing performed by the information processing unit 3, the CPU 31a first stores the received measurement data on the hard disk 31d (step S121).

The CPU 31*a* then executes a process to classify the particles in the sample using the measurement data (step S122). This process identifies the types of particles contained in the sample by the characteristic parameter information of the forward scattered light data, side scattered light data, and side fluorescent light data included in the measurement data.

Figure 8A:
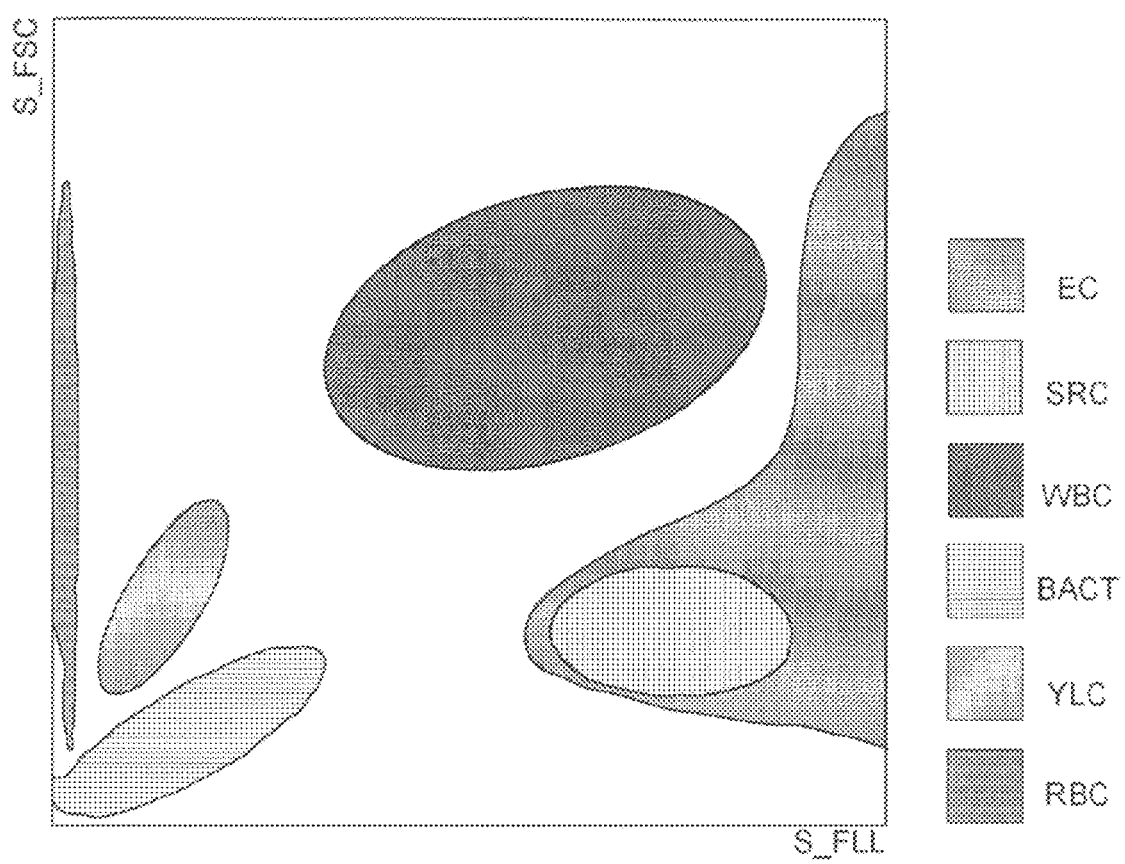
FIG. 8A is a scattergram which plots on the horizontal axis the fluorescent light intensity (low sensitivity) (FLL) obtained by measuring a first measurement sample, and plots on the vertical axis the forward scattered light intensity (FSC)
Figure 8B:
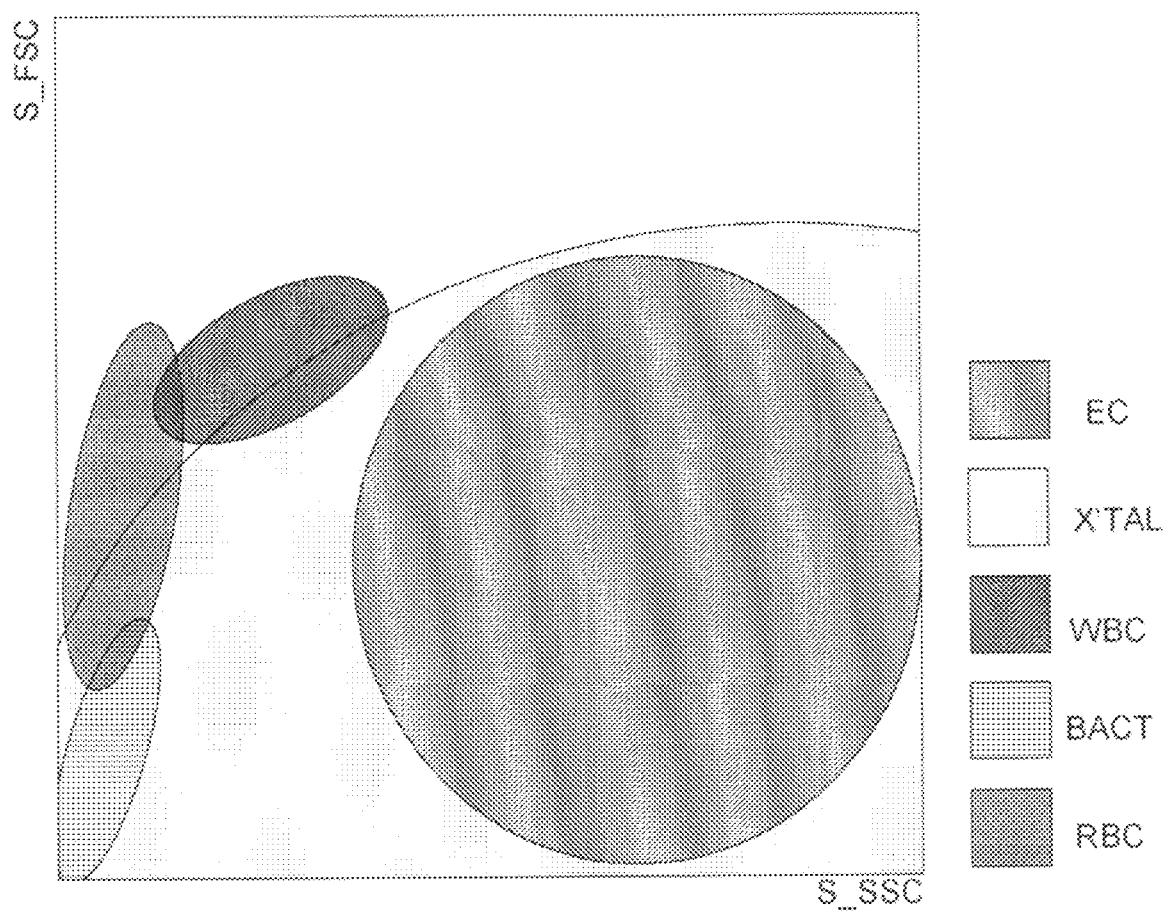
FIG. 8B is a scattergram which plots on the horizontal axis the side scatter light intensity (SSC) obtained by measuring the first measurement sample, and plots on the vertical axis the forward scattered light intensity (FSC)

This classification process is described in detail below. The tangible component in urine (SED) classification is performed based on the characteristic parameter information of the forward scattered light data, side scattered light data, and side fluorescent light data of the first measurement sample. FIG. 8A is a scattergram which plots on the horizontal axis the fluorescent light intensity (low sensitivity) (FLL) obtained by measuring a first measurement sample, and plots on the vertical axis the forward scattered light intensity (FSC). Epithelial cells (EC) and white blood cells (WBC) are large cells that have a nucleus and appear in regions that have a high fluorescent light signal intensity in the scattergram. The majority of epithelial cells are larger than white blood cells and appear in a region of higher fluorescent light intensity than white blood cells; however smaller epithelial cells overlap in the region in which white blood cells appear. The side scattered light data are used to discriminate between the two. FIG. 8B is a scattergram which plots on the horizontal axis the side scatter light intensity (SSC) obtained by measuring the first measurement sample, and plots on the vertical axis the forward scattered light intensity (FSC). As can be understood from the scattergram, epithelial cells appear in a region of higher side scattered light intensity than the white blood cells. Therefore, epithelial cells can be discriminated by the side scattered light intensity.

Figure 8C:
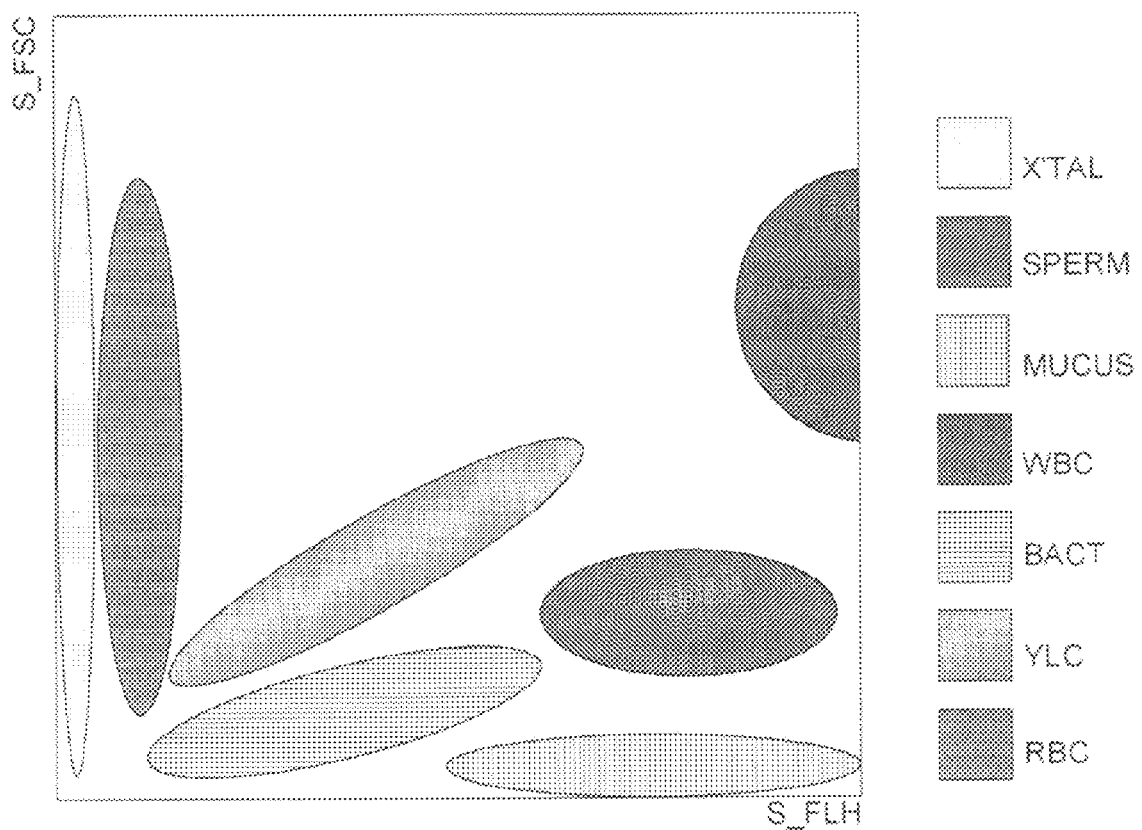
FIG. 8C is a scattergram which plots on the horizontal axis the fluorescent light intensity (high sensitivity) (FLH) obtained by measuring the first measurement sample, and plots on the vertical axis the forward scattered light intensity (FSC)

FIG. 8C is a scattergram which plots on the horizontal axis the fluorescent light intensity (high sensitivity) (FLH) obtained by measuring the first measurement sample, and plots on the vertical axis the forward scattered light intensity (FSC), and shows a region of low fluorescent light intensity. Red blood cells (RBC) are distributed in a region of low fluorescent light intensity since they do not have a nucleus. Since crystals appear in the region in which red blood cells appear, the side scattered light data are used to confirm the appearance of crystals. As shown in FIG. 8B, crystals appear in a large region and are not fixed to the center of the distribution of the side light intensity, therefore the red blood cells can be discriminated by the scattergram of FIG. 8C.

Figure 8D:
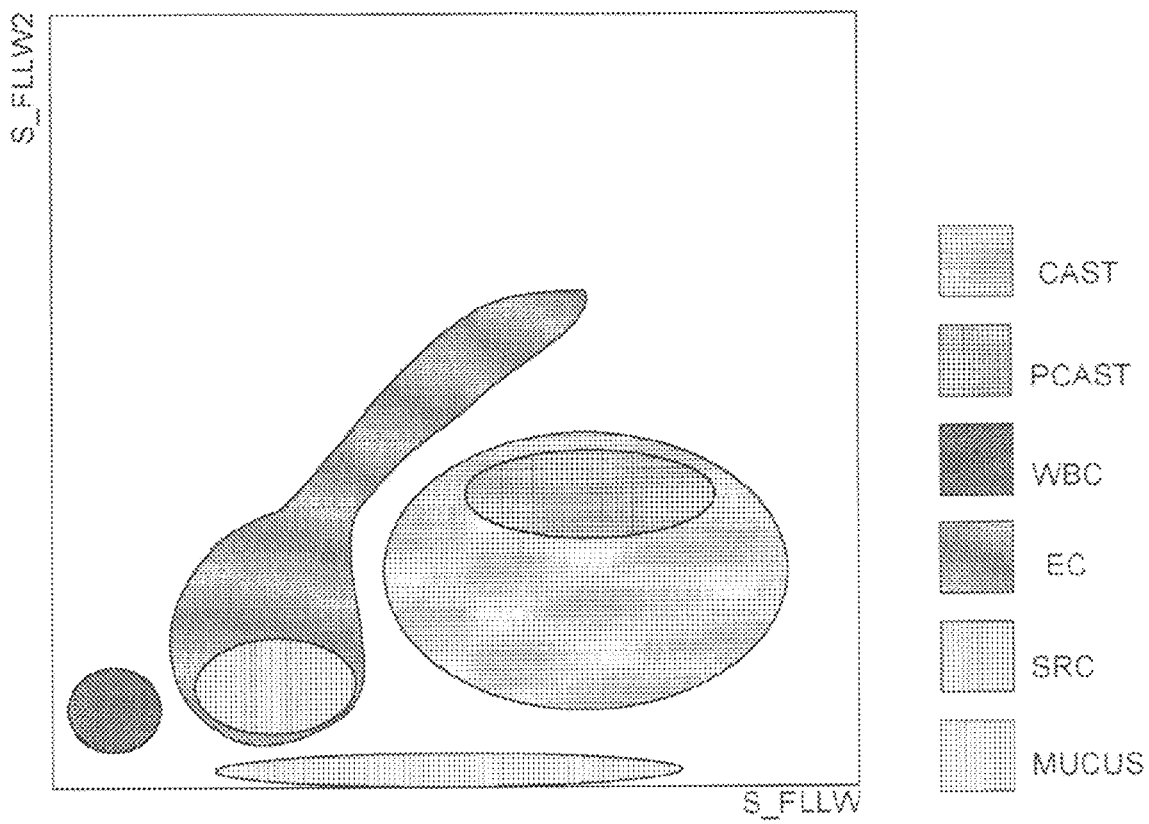
FIG. 8D is a scattergram which plots on the horizontal axis the fluorescent light signal width (fluorescent light width; FLLW) obtained by measuring the first measurement sample, and plots on the vertical axis a second fluorescent light width (fluorescent light width 2; FLLW2)

FIG. 8D is a scattergram which plots on the horizontal axis the fluorescent light signal width (fluorescent light width; FLLW) obtained by measuring the first measurement sample, and plots on the vertical axis a second fluorescent light width (fluorescent light width 2; FLLW2). The FLLW represents the width of the fluorescent light signal which captures the tangible component of the stained cell membrane, and the FLLW2 represents the width of the fluorescent light signal stronger than a nucleus. As shown in the drawing, the FLLW of urinary casts (CAST) is high, and the content of the cast (P.CAST) has a high FLLW2. The cast without content (CAST) appears in the region of low FLLW2. Thus, the cast with content and cast without content can be discriminated by the fluorescent light width and fluorescent light width 2.

Figure 8E:
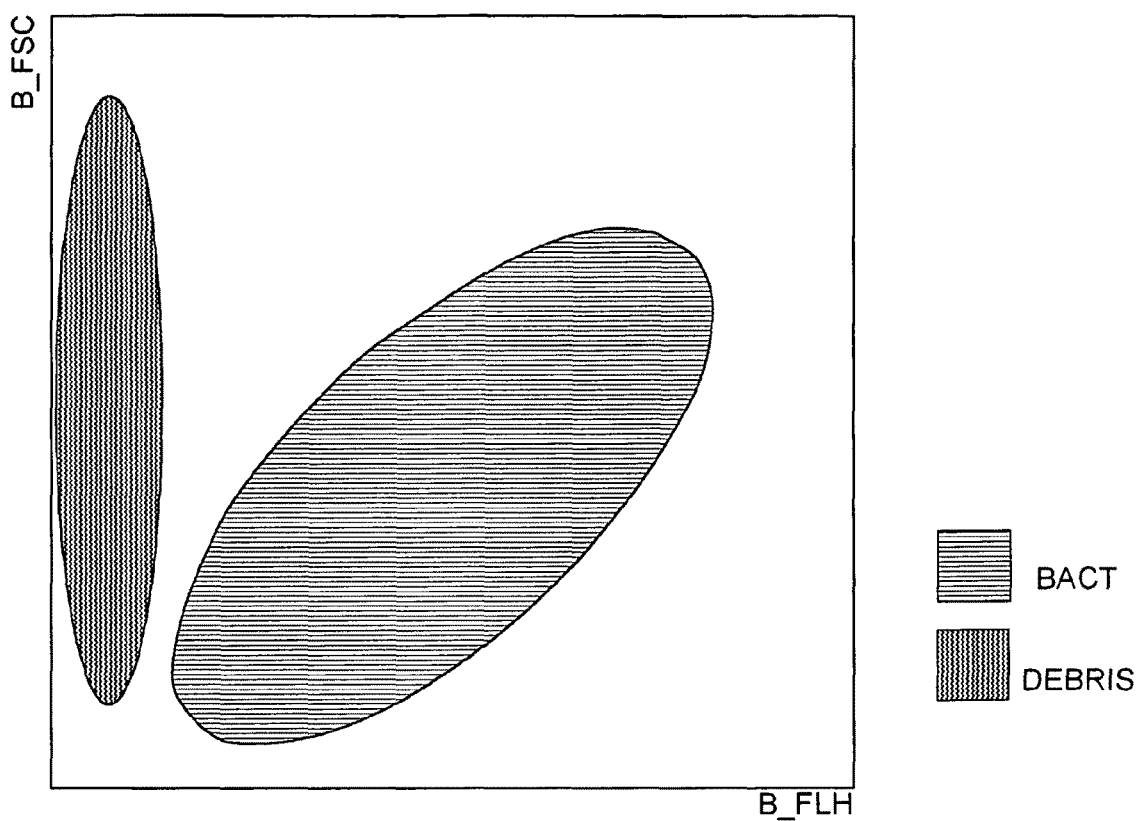
FIG. 8E is a scattergram which plots on the horizontal axis the fluorescent light intensity (high sensitivity) (B-FLH) obtained by measuring a second measurement sample, and plots on the vertical axis the forward scattered light intensity (high sensitivity) (B-=FSC)

The bacteria (BACT) classification (identification) is performed based on the characteristic parameter information of the forward scattered light data and fluorescent light data of the second measurement sample. FIG. 8E is a scattergram which plots on the horizontal axis the fluorescent light intensity (high sensitivity) (B-FLH) obtained by measuring a second measurement sample, and plots on the vertical axis the forward scattered light intensity (high sensitivity) (B-=FSC). As shown in the scattergram of FIG. 8C, the region of appearance of the bacteria overlaps the region of appearance of mucus threads (MUCUS), YLC (yeast like fungi), and SPERM (sperm) in the measurement of the tangible components in urine. In the bacteria measurement, however, since impurities such as mucus threads and red blood cell fragments are constricted by the bacteria measurement reagent used to prepare the second measurement sample, bacteria appear independently in a bacteria-only region and small bacteria can be detected with high accuracy because the measurement sensitivity is approximately 10 times greater than the measurement of the urine sediment; therefore accurate bacteria identification is possible by using the forward scattered light data and fluorescent light data of the second measurement sample.

This process classifies the particles detected by measuring the sample into red blood cells (RBC), white blood cells (WBC), epithelial cells (EC), casts (with content: P.CAST; without content: CAST), bacterium (BACT), crystals (X'TAL), mucus (MUCUS), yeast like fungi (YLC), sperm (SPERM), and impurities (DEBRIS). The data for displaying a scattergram to be described later are also generated by this classification process.

After the classification process, the CPU 31*a* executes a counting process to count the number of particles (step S123). In this process, a count is made of the number of each type of particle classified by the classification process. Then, the CPU 31*a* stores the count result of the counting process on the hard disk 31*d* (step S124).

Then the CPU 31*a* executes the process for anomaly determination (step S125). In the anomaly determination process, a determination is made as to whether a classification anomaly in particle classification process and a particle count anomaly in which the counted number of particles are not in the proper range has occurred.

Then the CPU 31*a* executes the process for creating a particle distribution diagram (step S126). In this process, data (hereinafter referred to as scattergram data) for displaying a scattergram and data (hereinafter referred to as histogram data) for displaying a histogram are prepared using the measurement data. The scattergram data prepared in this process are data for creating (1) a scattergram in which the fluorescent light intensity (low sensitivity) (FLL) obtained by measuring a first measurement sample is plotted on the horizontal axis and the forward scattered light intensity (FSC) is plotted on the vertical axis (refer to FIG. 8A); (2) a scattergram in which the fluorescent light intensity (high sensitivity) (FLH) obtained by measuring a first measurement sample is plotted on the horizontal axis and the forward scattered light intensity (FSC) is plotted on the vertical axis (refer to FIG. 8C); (3) a scattergram in which the width of the fluorescent light signal (FLLW) obtained by measuring a first measurement sample is plotted on the horizontal axis and the width of the second fluorescent light (florescent light width 2; FLLW2) is plotted on the vertical axis; and (4) a scattergram in which the fluorescent light intensity (high sensitivity) (B-FLH) obtained by measuring a second measurement sample is plotted on the horizontal axis and the forward scattered light intensity (high sensitivity) (B-FSC) is plotted on the vertical axis. The histogram data prepared in this process are data for creating (1) a histogram of red blood cells in which the frequency of appearance is plotted on the vertical axis and the forward scattered light intensity is plotted on the horizontal axis; and (2) a histogram of white blood cells in which the frequency of appearance is plotted on the vertical axis and the forward scattered light intensity is plotted on the horizontal axis. In the scattergrams, each of the particles is displayed as color-coded particles according to type (for example, red blood cells are displayed in red, and white blood cells in blue). The scattergram data therefore includes information of the color of each particle.

The CPU 31a then stores the analysis results data including the above classification results, count results, anomaly determination result, scattergram data, histogram data, and attribute information including the sample ID, patient ID, patient name, age, sex, department, attending physician included in the measurement order of this sample on the hard disk 31d (step S127). The analysis result database 37 is a relational database provided with fields for sample ID, sample analysis date, patient ID, patient name, age, sex, department, attending physician, classification result, count result, anomaly determination result, scattergram data, and histogram data. Each record corresponds to the analysis result of one sample, and new records are added to the analysis result database 37 when an analysis result has been generated by the above process. After the analysis result data have been recorded to the analysis result database 37, the CPU 31a returns the process to the call address of the measurement data process of step S115 in the measurement data analysis operation (main routine).

After the measurement data process S115 ends, the CPU 31a generates an interrupt request to display the analysis result screen. When the display request for the analysis result screen has been generated, the CPU 31a first generates the analysis result screen based on the analysis result data (step S116). In this process, bit-map type image data of the scattergram and histogram are respectively generates based on the scattergram data and histogram data.

The CPU 31a then retrieves the comment to be displayed on the analysis result screen (step S117). The comment retrieval process is described in details below. In the comment retrieval process, comments are retrieved using the comment retrieval database 36 provided on the hard disk 31d. FIG. 9 is a schematic view showing the structure of the comment retrieval database 36. The comment retrieval database 36 is a relational database provided with fields including item 36a corresponding to a comment, content actual data) 36b of information of the item displayed on the analysis result screen, reading authority setting value 36c, and comment 36d. Each record corresponds to one comment; the user inputs the item corresponding to the comment, actual data of the item, user group of the reading object, and the comment in the comment input dialog which will be described later, and a new record that includes this input information is added to the comment retrieval database 36.

The field 36a of the item corresponding to the comment records one of the [sample ID], [patient ID], [attending physician], [department], [particle distribution diagram (scatter S1)], [particle distribution diagram (scatter S2)], [particle distribution diagram (scatter S3)], [particle distribution diagram (scatter B1)], [particle distribution diagram (scatter (RBC-S_FSC)], and [particle distribution diagram (WBC-S_FSC)]. Whether the record of the comment corresponds to an item of the analysis result screen can be identified by the data recorded in field 36a.

Textual data of the items [sample ID], [patient ID], [attending physician], [department], or [reference information] in the analysis result data for are recorded in field 36b of the actual data of the item corresponding to the comment. For example, when the [sample ID] is [0001] and recorded in the item field 36b, the text [0001] is recorded in field 36b. Further, when the [department] is [urology] and recorded in the item field 36b, the text [urology] is recorded in field 36b. When the item is any particle distribution diagram, the bit-map image data of the particle distribution diagram are recorded in the field 36b. For example, when [particle distribution diagram (scatter S1)] is recorded in the item field 36b, the image data of [particle distribution diagram (scatter S1)] are recorded in field 36b.

One or more group of the user groups [unrestricted], [chief technologist], [managing technologist], [technologist], [nurse], [serviceman], [administrator], [physician] is recorded in the reading authority setting field 36c. The data recorded in field 36c determines the reading authority for the comment of this record relative to the user group to which the currently logged in user belongs. For example, when [unrestricted] is recorded in the record of the comment, users belonging to any group can read the comment. Similarly, when [chief technologist], [managing technologist], [technologist], [nurse], [serviceman], [administrator], or [physician] is recorded in the record of the comment, a user belonging to the user group [chief technologist], [managing technologist], [technologist], [nurse], [serviceman], [administrator], or [physician], respectively, has reading authority.

Text data of a user-input comment are recorded in the comment field 36d.

Figure 10:
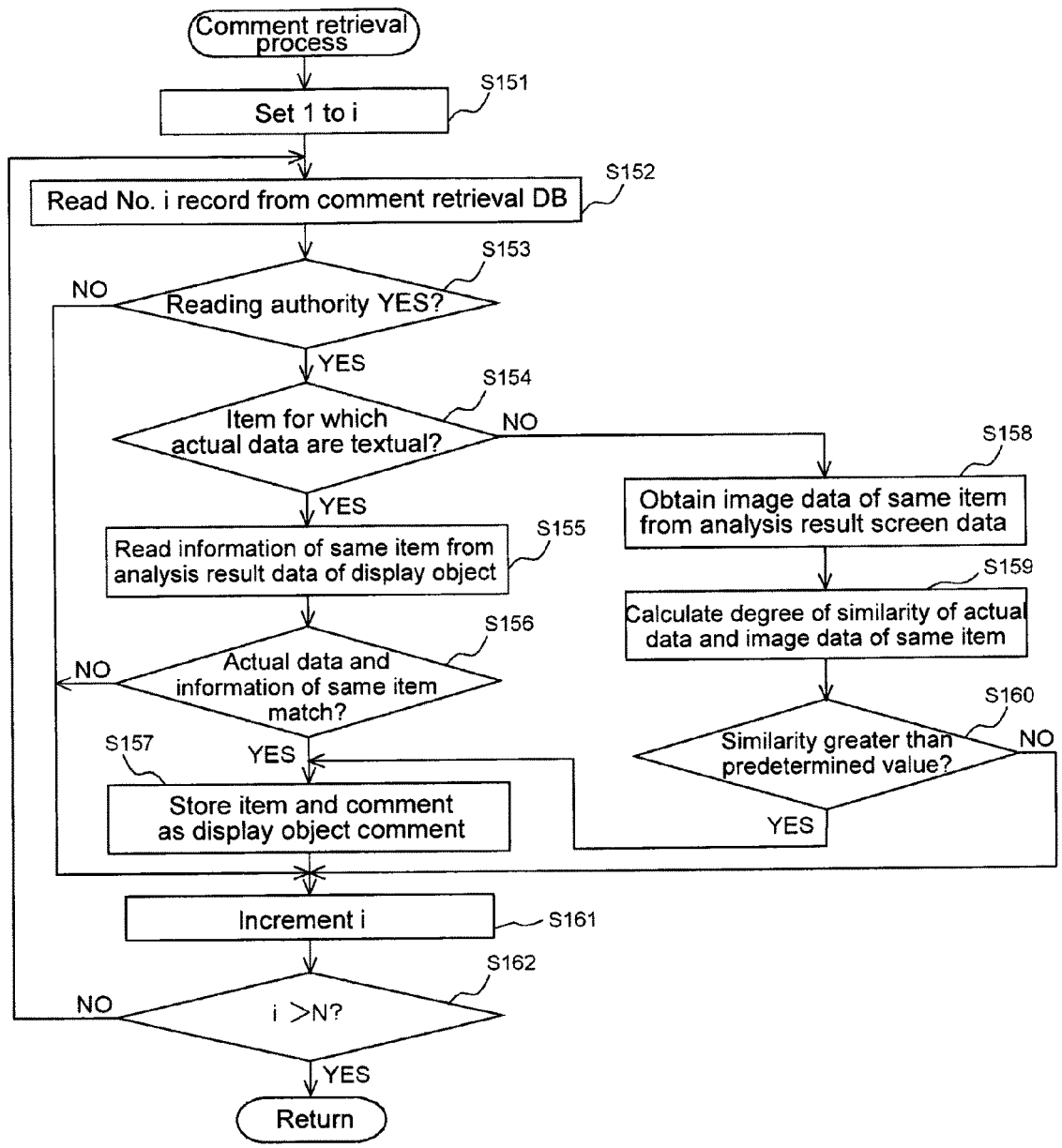
FIG. 10 is a flow chart showing the sequence of the comment retrieval process.

FIG. 10 is a flow chart showing the sequence of the comment retrieval process. The CPU 31a first sets the variable i to [1] (step S151), and reads the number i record from the top of the comment retrieval database 36 (step S152). Then the CPU 31a compares the user group of the currently logged in user and the setting value of the reading authority of the read record to determine whether the user has reading authority (step S153). When the user does not have reading authority (step S153: NO), the CPU 31a moves the process to step S161.

When the user has reading authority in step S153 (step S153: YES), the CPU 31a determines whether the item of the read record is [sample ID], [patient ID], [attending physician], [department], or [reference information] (the item for which actual data are textual) (step S154).

When the item is [sample ID], [patient ID], [attending physician], [department], or [reference information] in step S154 (step S154: YES), the CPU 31a determines whether the two data match by reading the item of the read record (for example, [patient ID] with item information of, for example [0002]) from the analysis result data of the display object (step S155), and comparing the actual data (for example [0001]) read from the comment retrieval database 36 and the information read in step S155. When the two data do not match (step S156: NO), the process moves to step S161.

When the two data match in step S156 (step S156: YES), the CPU 31a stores the comment and item included in the record read from the comment retrieval database 36 in RAM 31c as a display object comment (step S157).

On the other hand, when the item is not [sample ID], [patient ID], [attending physician], [department], or [reference information], that is, when the item is [particle distribution diagram (scatter S1)], [particle distribution diagram (scatter S2)], [particle distribution diagram (scatter S3)], [particle distribution diagram (scatter B1)], [particle distribution diagram (RBC-S_FSC)], or [particle distribution diagram (WBC-S_FSC)] (the item is the actual data of the image data) in step S154 (step S154: NO), the CPU 31a obtains the image data of the same item, for example, [particle distribution diagram (scatter S1)] from the bit-map image data created in step S116 (step S158). The CPU 31a calculates the degree of similarity of the two image data by comparing, via pattern-matching, the actual data (bit-map image data) read from the comment retrieval database 36 and the image data obtained in step S158. When the CPU 31a compares the degree of similarity and a predetermined value (step S160) and the degree of similarity of the two image data is less than the predetermined value (step S160: NO), the process moves to step S161.

When the degree of similarity is equal to or greater than the predetermined value in step S160 (step S160: YES), the CPU 31a moves the process to step S157 and stores the comment and item included in the record read from the comment retrieval database 36 in RAM 31c as a display object comment.

After the display object comment has been stored in step S157, the CPU 31a increments i by [1] (step S161), and determines whether i is greater than the record number N of the comment retrieval database 36 (step S162). When i<N (step S162: NO), the CPU 31a returns to step S152. When i>N in step S162, the CPU 31a returns the process to the call address of the comment retrieval process S117 in the measurement data analysis operation (main routine).

Figure 11:
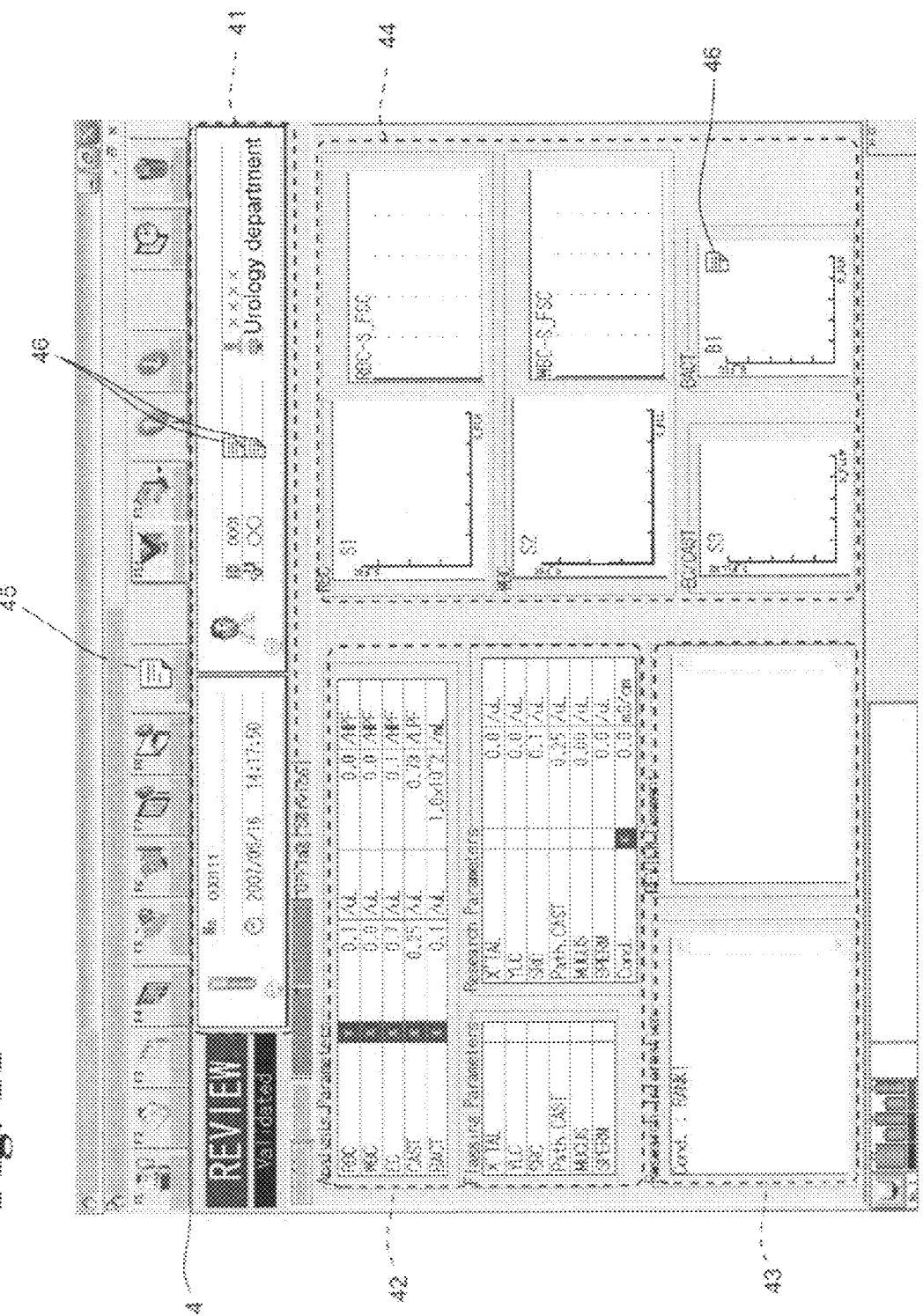
FIG. 11 is a schematic diagram showing an example of the analysis result screen.

After the comment retrieval process S117 ends, the CPU 31a displays the analysis result screen prepared in step S116 on the image display 32 (step S118). FIG. 11 is a schematic diagram showing an example of the analysis result screen. The analysis result screen 4 includes a sample attribute information display part 41, numerical data display part 42, reference information display part 43, and particle distribution diagram display part 44. The sample attribute information display part 41 displays attribute information such as the sample ID, sample analysis date, patient ID, patient name, department, attending physician and the like. Numerical value data of the analysis result, that is, red blood cell count, white blood cell count, epithelial cell count, cast count, bacteria count and other numerical values are displayed in the numerical data display part 42. The content of an anomaly is display in text in the reference information display part 43 when a classification anomaly or particle count anomaly has been detected. The particle distribution diagram display part 44 displays six particle distribution diagrams, including (1) a scattergram in which the fluorescent light intensity (high sensitivity) (FLH) obtained by measuring a first measurement sample is plotted on the horizontal axis and the forward scattered light intensity (FSC) is plotted on the vertical axis (scattergram of FIG. 8C; hereinafter referred to as scattergram S1); (2) a scattergram in which the fluorescent light intensity (low sensitivity) (FLL) obtained by measuring a first measurement sample is plotted on the horizontal axis and the forward scattered light intensity (FSC) is plotted on the vertical axis (scattergram of FIG. 8A; hereinafter referred to as scattergram S2); (3) a scattergram in which the width of the fluorescent light signal (FLLW) obtained by measuring a first measurement sample is plotted on the horizontal axis and the width of the second fluorescent light (florescent light width 2; FLLW2) is plotted on the vertical axis (scattergram of FIG. 8D; hereinafter referred to as scattergram S3); (4) a scattergram in which the fluorescent light intensity (high sensitivity) (B-FLH) obtained by measuring a second measurement sample is plotted on the horizontal axis and the forward scattered light intensity (high sensitivity) (B-FSC) is plotted on the vertical axis (scattergram of FIG. 8E; hereinafter referred to as scattergram B1); (5) histogram of red blood cells in which the appearance frequency is plotted on the vertical axis and the forward scattered light intensity is plotted on the horizontal axis (hereinafter referred to as RBC histogram); and (6) a histogram of white blood cells in which the appearance frequency is plotted on the vertical axis and the forward scattered light intensity is plotted on the horizontal axis (hereinafter referred to as WBC histogram).

When there is a comment to be displayed in the analysis result screen, that is, when item data and comment data are stored in the RAM 31c, a comment icon 46 is displayed near the item to which the comment is related in the analysis result screen. The comment icon 46 indicates that the comment can be displayed for the item t the displayed location. As previously described, the comment corresponding to the item is displayed when the user aligns the mouse cursor with the comment icon 46.

The comment retrieval database 36 for comment retrieval is provided independently of the analysis result database 37 so that comment retrieval can be performed efficiently at high speed by retrieving the comment to be displayed using the comment retrieval database 36.

In this state, when the user performs an operation to issue a display end instruction for the analysis result screen by clicking an end button displayed on the analysis result screen or the like, the CPU 31a receives the display end instruction for the analysis result screen (step S119), generates an interrupt request, and the CPU 31a ends the display of the analysis result screen (step S120), whereupon the process ends.

The analysis result screen is not only displayed after the sample measurement and measurement data processing ends as described above, the analysis result screen may also be displayed when a user has specified analysis results from among past analysis result to be displayed by sample number or the like. In this case, the comment retrieval process of step S117 is executed before displaying the analysis result screen corresponding to the specified sample number.

The sample analyzer 1 of the present embodiment can display comments when the analysis result screen is being displayed as described above. The comment display process is described in detail below.

Figure 12:
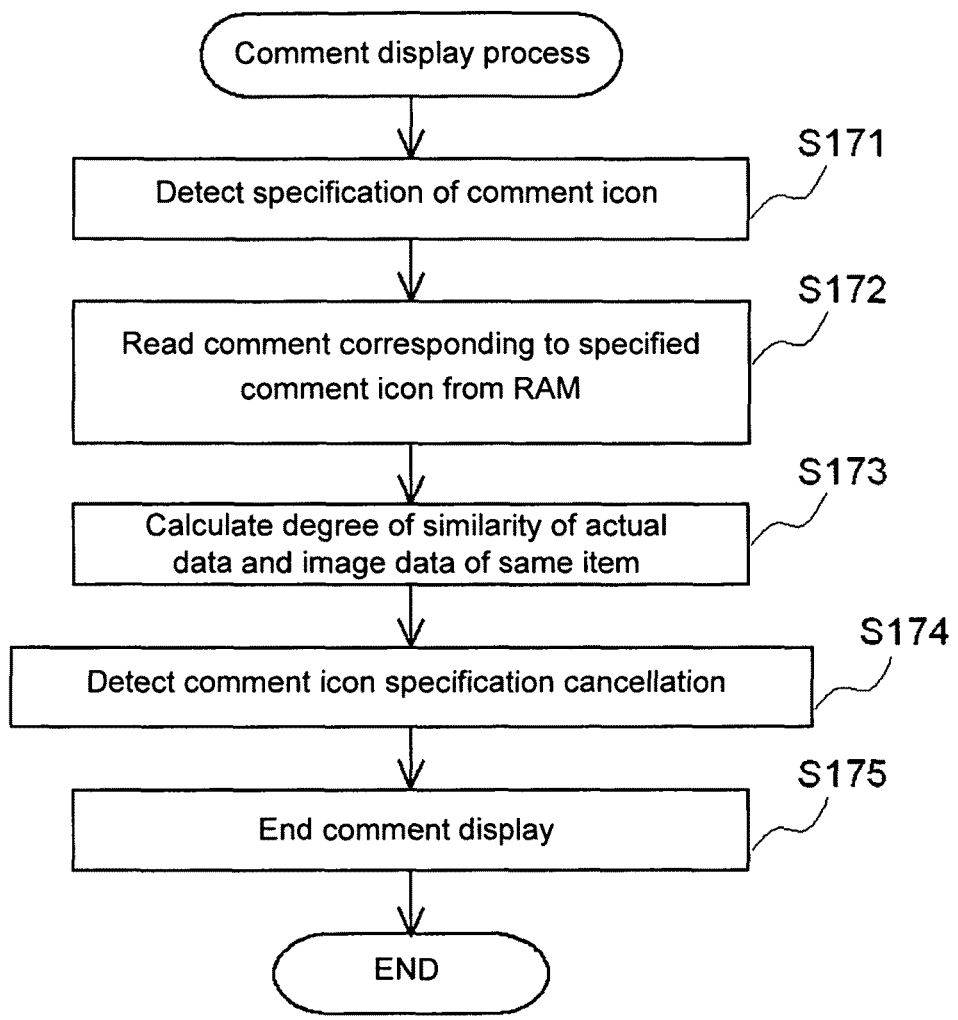
FIG. 12 is a flow chart showing the sequence of the comment display process.

FIG. 12 is a flow chart showing the sequence of the comment display process. When the analysis result screen is displayed on the image display part 32, the CPU 31a of the information processing unit 3 determined whether the comment icon 46 has been specified (step S171). This specification is performed by the user operating a mouse included in the input part 33 to overlay the mouse cursor (pointer) on the comment icon 46. That is, the determination process of step S171 is performed by determining whether the mouse cursor is overlaid on the comment icon 46. When the specification of the comment icon 46 has been detected, the CPU 31a then generates an interrupt request and calls the process of step S172 below.

Figure 13:
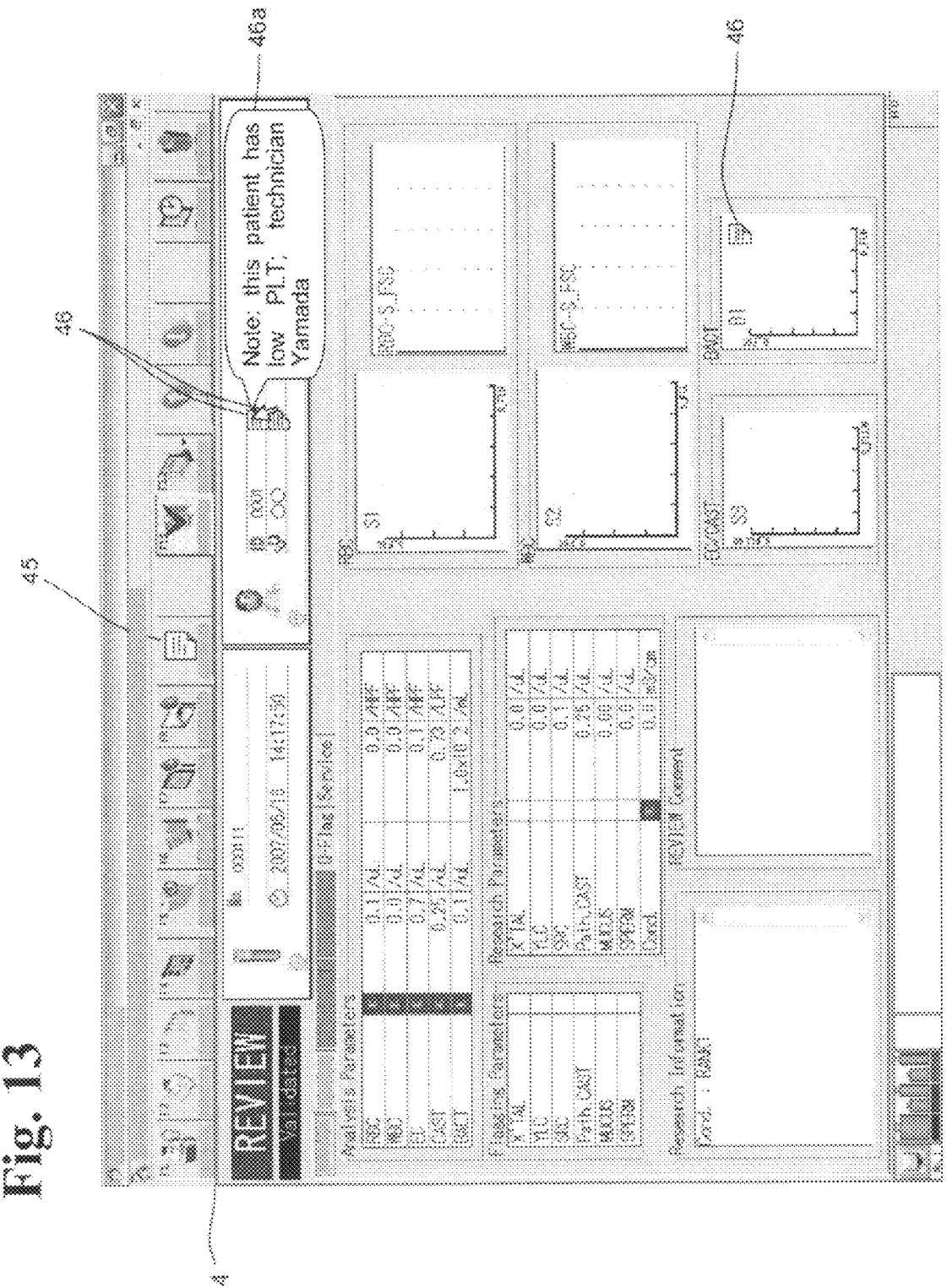
FIG. 13 shows an example of the analysis result screen which displays the comment in a pop-up.

In step S172, the CPU 31a reads the comment of the item corresponding to the specified comment icon 46 from the RAM 31c (step S172). The CPU 31a then displays the comment in a pop-up (step S173). The analysis result screen displaying the comment is described below. FIG. 13 shows an example of the analysis result screen which displays the comment in a pop-up. FIG. 13 shown an example in which a comment related to the [patient ID] item is displayed. In this example, comment icons 46 are respectively displayed for [patient ID], [attending physician], [and [particle distribution diagram (scatter B1)] in the analysis result screen 4. When the user specifies the comment icon 46 displayed near the item [patient ID], the comment 46a [Note: this patient has low PLT; technician Yamada] corresponding to the patient ID [0001] is displayed. The comment 46a is displayed in a square balloon displayed when the comment icon 46 is specified, and the balloon is displayed so that the patient ID display position is indicated, that is, so that the end of the acute part of a triangle protruding from the balloon is positioned at the display position. In this example, the sample analyzer 1 has a single user, and the technician Yamada, who has detailed knowledge of the patient, has input the comment. The comment is a past comment input by the knowledgeable technician Yamada. Insofar as the user has comment reading authority, the comment icon 46a is displayed in all analysis result screens matching the patient ID of [0001]. Therefore, when a user other than technician Yamada is logged in and the analysis result screen 4 is displayed, the user who lacks detailed knowledge of the individual patient can easily obtain specific information of the patient, and know that there is no anomaly even when an analysis result is displayed which indicates a lower than normal PLT (platelet) count because the patient tends to have low PLT. In other words, detailed information of an individual patient known to a single user (technician Yamada) can be easily shared among a plurality of users.

When the attending physician inputs [fast result desired] as a comment, the comment related to physician [oo] is displayed, and a user who reads the comment will know that a fast analysis result is required. When [staphylococcus?] is entered as a comment for [particle distribution diagram (scatter B1)], the comment is displayed when the scattergram B1 displayed on the analysis result screen is similar to the stored scattergram B1 associated with the comment in the comment retrieval database 36. Although skill is required to comprehend the condition of the patient when observing a scattergram, the knowledge of skilled users can be shared because the content determined by a skilled user when referencing the scattergram is displayed when a scattergram similar to the stored scattergram is displayed as an analysis result. Furthermore, an inexperienced user can be taught by displaying such comments when the inexperienced user who lacks a deep skill-set references the analysis result screen.

A user can reference the comment and analysis result (including attribute information) simultaneously by displaying the analysis result screen 4 with the added comment 46a, and the content of the analysis result and the content of the comment can be associated, understood, and stored.

When CPU 31a detects that the mouse cursor has moved away from the comment icon 46 (the specification of the comment icon 46 is cancelled), the CPU 31a generates an interrupt request, ends the comment display (step S175), and the process ends.

The sample analyzer 1 of the present embodiment is also capable of receiving comment input (record) when the analysis result screen is being displayed as described above. The comment recording process is described in detail below.

Figure 14:
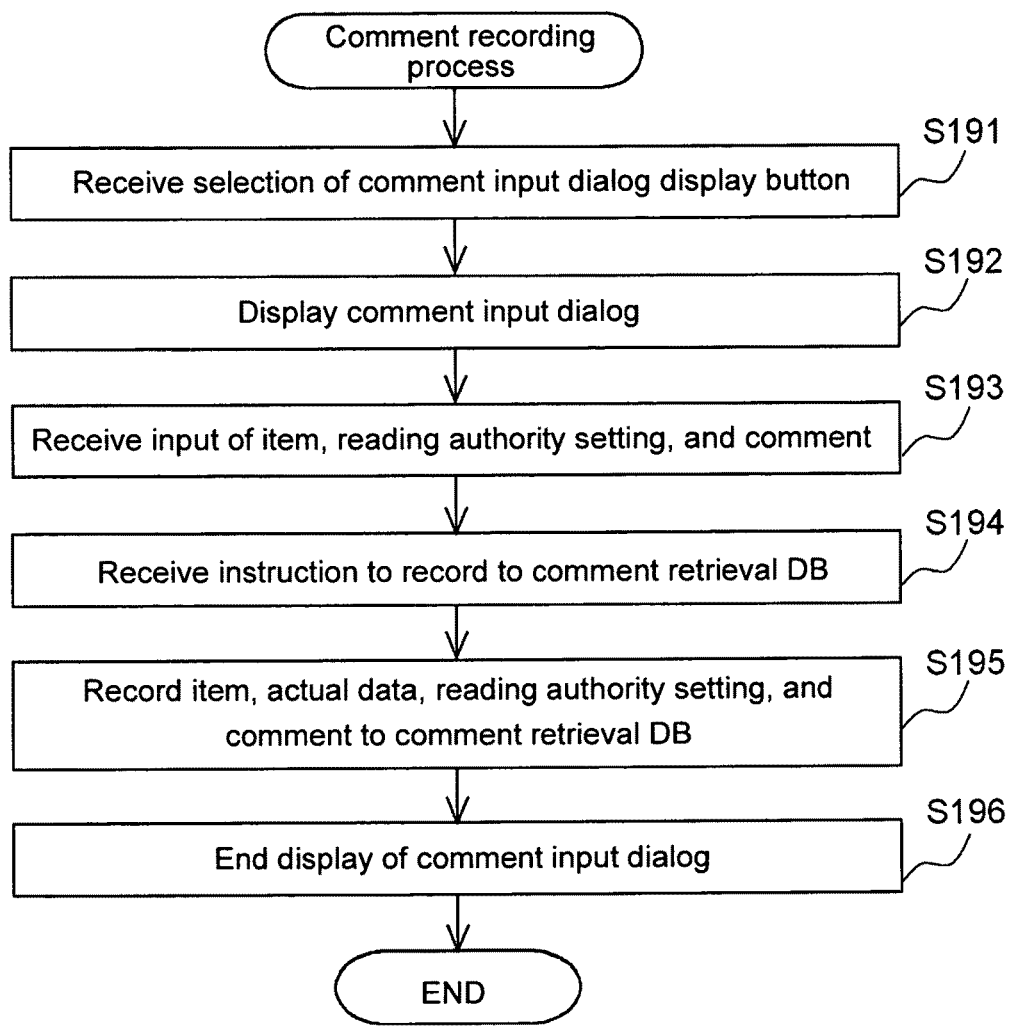
FIG. 14 is a flow chart showing the sequence of the comment recording process of the sample analyzer of the first embodiment.

FIG. 14 is a flow chart showing the sequence of the comment recording process. As shown in FIG. 11, the analysis result screen 4 is provided with a comment input dialog display button 45 for calling the comment input dialog. When the comment input dialog display button 45 is clicked, a comment is executed to display the comment input dialog. When the CPU 31a receives the instruction resulting from the operation of the user clicking the comment input dialog (step S191), the CPU 31a generates an interrupt request and calls the process of step S192.

Figure 15:
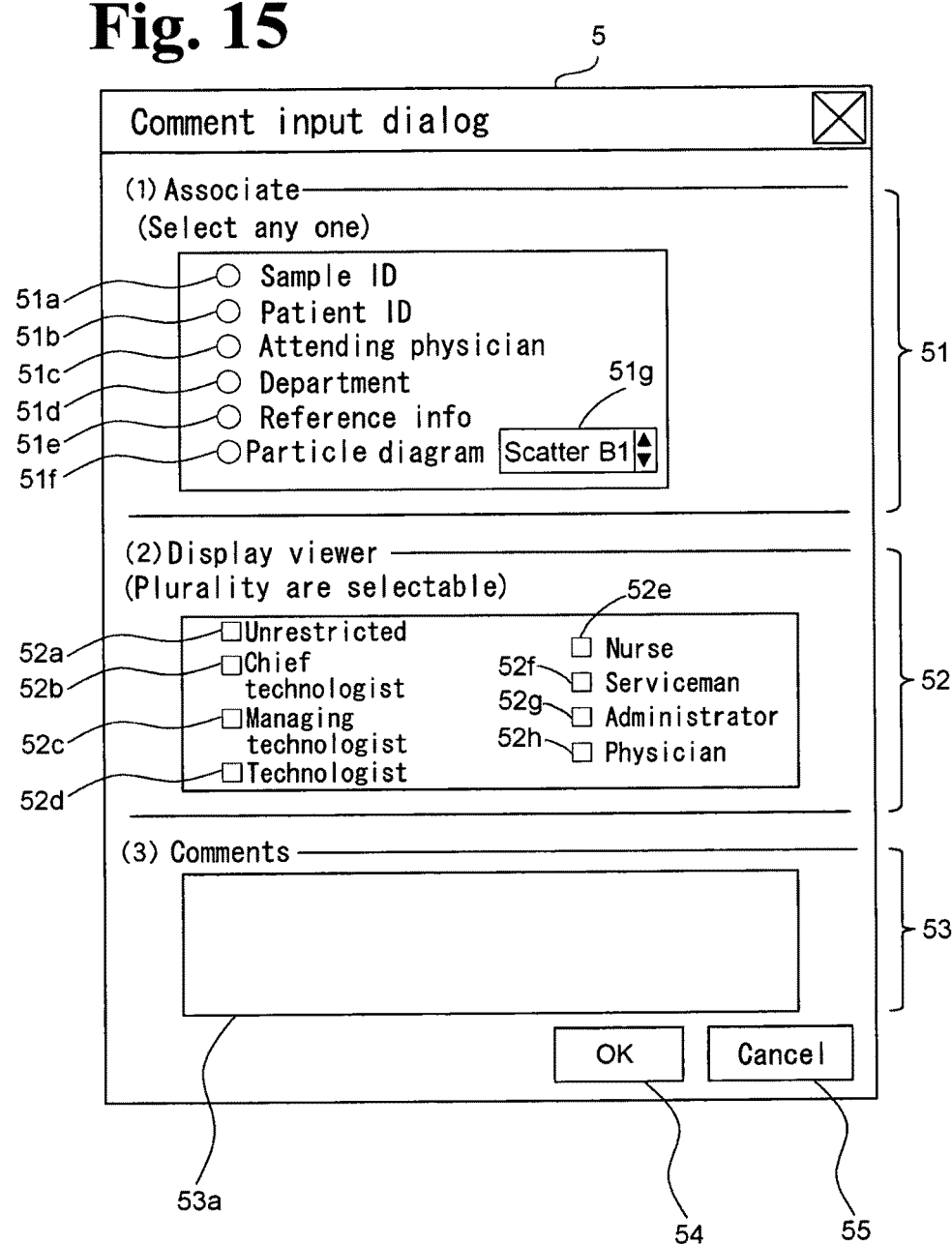
FIG. 15 is a schematic diagram showing an example of the comment input dialog.

In step S192, the CPU 31a displays the comment input dialog on the image display part 32. FIG. 15 is a schematic diagram showing an example of the comment input dialog. The comment input dialog 5 is provided with an item specification region 51 for specifying an item associated with a comment, reading object specification region 52 for specifying the user group of a comment reading object, comment input region 53 for inputting a comment, OK button 54 for confirming the input content after the comment has been input, and a cancel button 55 for canceling the comment input process. Six selections including [sample ID], [patient ID], [attending physician], [department], [reference information], and [particle distribution diagram] are displayed in the item specification region 51. Radio buttons 51a through 51f are respectively provided to the left of the six selections [sample ID], [patient ID], [attending physician], [department], [reference information], and [particle distribution diagram]. A corresponding (displayed to the right of the radio button) selection can be selected by the user selecting (clicking) any of the radio buttons 51a through 51f. A specification box 51g is displayed on the right side of the selection [particle distribution diagram], and this specification box 51g can be used to specify a scattergram or histogram as the comment input object. For example, to specify the scattergram B1, the user performs an operation to display [scatter B1] in the specification box 51g. When the radio button 51f is selected, the scattergram or histogram specified in the specification box 51g is set as the comment input object.

The reading object specification region 52 displays eight selections including [unrestricted], [chief technologist], [managing technologist], [technologist], [nurse], [serviceman], [administrator], and [physician]. A single checkbox 52a through 52h is displayed on the right side of these eight selections. A plurality of these selections may be selected at the same time. The user selects a selection corresponding to a checkbox by selecting (clicking) one or more of the checkboxes 52a through 52h. A comment reading authority input in the comment input region 53 is assigned to the selected user group.

An input box 53a for inputting a comment is displayed in the comment input region 53. When a click operation is performed inside the input box 53a, a cursor is displayed and text can be input. In this state, the user can input a comment as text data.

When a user inputs an item selection, reading authority setting, or comment in the comment input dialog 5 described above, the CPU 31a receives the input information (step S193). When the user clicks the OK button 54, the CPU 31a receives the instruction to record the comment in the comment retrieval database 36. When the CPU 31a receives the comment record instruction (step S194), the CPU 31a generates an interrupt request and records the item, reading authority setting, and comment received in step S193, and the information (actual data) corresponding to the item displayed in the analysis result screen in the comment retrieval database 36 (step S195). For example, when [reference information] is selected in items, [unrestricted] is selected as the user group for reading authority, and [threshold value for determining sharing not governed by patient information as universal] is input in the comment in the comment input dialog 5 called when the analysis result screen is displayed with [universal] showing in the reference information, [reference information] is recorded in the [item] field 36a, [universal] is recorded in the [actual data] field 36b, [unrestricted] is recorded in the [reading authority] field 36c, and [threshold value for determining sharing not governed by patient information as universal] is recorded in the [comment] field 36d of the comment retrieval database 36.

The CPU 31a then ends the display of the comment input dialog 5 (step S196), and the process ends. When the cancel button 55 is clicked, the input information is deleted and the display of the comment input dialog 5 ends.

Second Embodiment

The present embodiment is a sample analyzer for automatically selecting an [item] in a comment input dialog.

In the sample analyzer of the present embodiment, when a user wants to add a comment to an item in the analysis result screen, the comment input dialog 5 is displayed by a predetermined operation for specifying the region in which the item is displayed, for example, by double clicking the left mouse button or clicking the right mouse button within the region. The comment input dialog 5 is displayed in a state in which an item corresponding to the user-specified region is pre-selected in the item specification region 51 (refer to FIG. 15). The structure of the sample analyzer of the present embodiment is identical to the structure described in the first embodiment and further description is therefore omitted.

Figure 16:
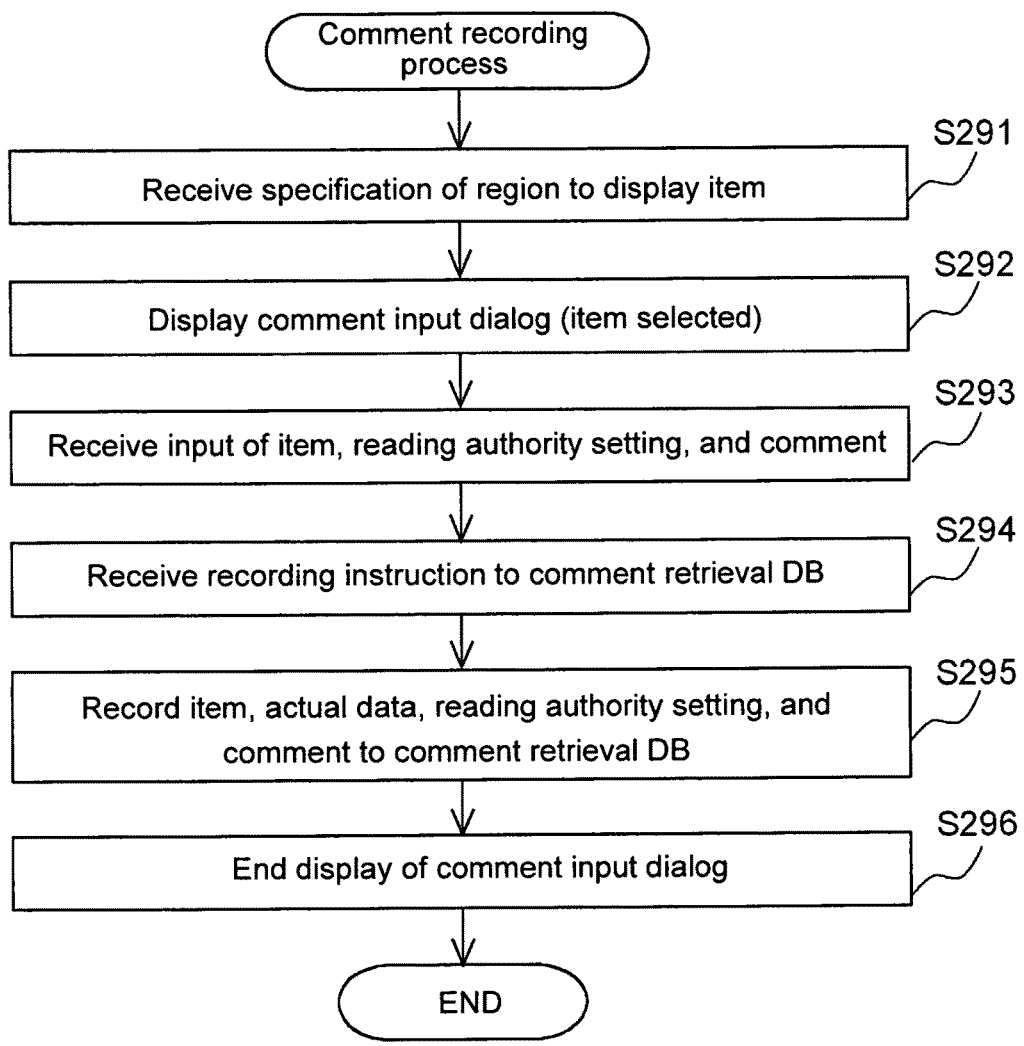
FIG. 16 is a flow chart showing the sequence of the comment recording process of the sample analyzer of the second embodiment.

The operation of the comment recording process of the sample analyzer of the present invention is described below. FIG. 16 is a flow chart showing the sequence of the comment recording process of the sample analyzer of the present embodiment. When the user performs an operation specifying any of the display regions [sample ID], [patient ID], [attending physician], [department], [reference information], [particle distribution diagram (scatter S1)], [particle distribution diagram (scatter S2)], [particle distribution diagram (scatter S3)], [particle distribution diagram (scatter B1)], [particle distribution diagram (RBC-S_FSC)], or [particle distribution diagram (WBC-S_FSC)] (step S291), the CPU 31a generates an interrupt request and calls the process of step S292.

In step S292, the CPU 31a displays the comment input dialog on the image display part 32. The comment input dialog 5 is displayed with the items corresponding to the user-selected region in a pre-selected state in the item specification region 51. For example, when the user positions the mouse cursor on the reference information display part 43 (refer to FIG. 11) of the analysis result screen 4, the comment input dialog 5 is displayed with the [reference information] radio button 51e selected in the item specification region 51 by double-clicking the left mouse button. In the comment input dialog 5, the user can cancel the selection of the automatically selected item so as to select another item. The input of the comment and reading authority setting are performed identically to the first embodiment.

Since the processes of steps S293 through S296 are identical to the steps S193 to S196 of the comment recording process of the first embodiment, further description is omitted.

The structure described above provides that a user can simultaneously select an item in the comment input dialog and display the comment input dialog by simply performing an operation to specify the region to display the information of the item for which a comment is desired, thus improving the user operationality of the sample analyzer.

Other Embodiments

Note that although the above embodiments are described in terms of displaying the comment when the text data information of the item in the analysis result of the display object matches the content (actual data) of the item information corresponding to the comment in the comment retrieval database and the items corresponding to a comment being [sample ID], [patient ID], [attending physician], [department], and [reference information], the present invention is not limited to this arrangement. The comment can also be displayed even when the text data included in the analysis result of the display object and the actual data (text data) recorded in the comment retrieval database do not match but are similar. In this case, similarity can be determined when the number of letters which match in both compared data is greater than a predetermined value, or similarity can be determined when the number of matching letters is greater than a fixed ratio. It is also possible to determined whether there is similarity using pre-recorded similar text dictionary data (for example, hiragana having the same reading as kanji may be recorded as similar).

Although the above embodiments are described in terms of displaying a comment when a calculated similarity is greater than a predetermined value determined by pattern matching the degree of similarity of the image data information item in the analysis result of a display object and the image data corresponding to the comment in the comment retrieval database and the items corresponding to the comment being [particle distribution diagram (scatter S1)], [particle distribution diagram (scatter S2)], [particle distribution diagram (scatter S3)], [particle distribution diagram (scatter B1)], [particle distribution diagram (scatter RBC-S_FSC)], or [particle distribution diagram (scatter WBC-S_FSC)], the present invention is not limited to this arrangement. When recording a comment relating to a particle distribution diagram, the characteristic data of a particle distribution diagram such as the center position of each cluster in a scattergram which is the object of the comment, the data indicating the direction in which a particle group appears and extends in the scattergram, and/or the position of the peaks in a histogram may be recorded as actual data, the characteristic data of the particle distribution diagram in the analysis result of the display object may be extracted and both characteristic data may be compared to calculate the degree of similarity, or determine whether both characteristic data match or are similar.

Although the above embodiments are described in terms of inputting a comment to an item by selecting one item from the items of [sample ID], [patient ID], [attending physician], [department], [reference information], [particle distribution diagram (scatter S1)], [particle distribution diagram (scatter S2)], [particle distribution diagram (scatter S3)], [particle distribution diagram (scatter B1)], [particle distribution diagram (scatter RBC-S_FSC)], or [particle distribution diagram (scatter WBC-S_FSC)], the present invention is not limited to this arrangement. Predetermined information in the analysis result, for example, only the scattergram S1, can be pre-defined as a comment input object, so as to record and display only the comment relating to the predetermined information.

Although the above embodiment have been described in terms of retrieving a comment to be displayed using a retrieval database when a comment retrieval database to be used for comment retrieval has been pre-stored on a hard drive, the present invention is not limited to this arrangement. When a comment and field of an item corresponding to the comment are provided in an analysis result database and a comment has been input when the analysis result screen is displayed, the comment and item may also be added to the record of the analysis result data. In this case, the comment to be displayed can be retrieved using the item and the actual data corresponding to the item in the analysis result database. Also in this case, a plurality of comments and item fields may be provided in the analysis result database. A plurality of comments corresponding to one analysis result can then be recorded in this way.

Although the above embodiments are described in terms of displaying a comment when a calculated similarity is greater than a predetermined value determined by pattern matching the degree of similarity of the image data of an information item in the analysis result of a display object and the image data corresponding to the comment in the comment retrieval database and the items corresponding to the comment being [particle distribution diagram (scatter S1)], [particle distribution diagram (scatter S2)], [particle distribution diagram (scatter S3)], [particle distribution diagram (scatter B1)],

[particle distribution diagram (scatter RBC-S_FSC)], or [particle distribution diagram (scatter WBC-S_FSC)], and the text of an information item in the analysis result of the display object matches the content (actual data) of the information item corresponding to the comment in the comment retrieval database, and the items corresponding to a comment are [sample ID], [patient ID], [attending physician], [department], or [reference information], the present invention is not limited to this arrangement. A comment may also be displayed when predetermined information included in the analysis result information of the display object meets a predetermined condition. For example, the comment may also be displayed when the classification of the item information corresponding to the comment matches the classification of the item information in the analysis result of the display object and the information of the classification of the classified item information (actual data) is pre-stored for each item. Specifically, when the [male in 40s] is used as a classification of the patient ID of the analysis result related to the comment, the comment may also be displayed when displaying the analysis result information which has a patient ID classification that matches the [male in 40s] classification of the patient ID related to the comment. The comment may also be displayed when supplemental information of the item information corresponding to the comment matches information supplementing the item information in the analysis result of the display object and the information supplementing the item information is included in the analysis result information beforehand. Specifically, in the case wherein the a comment is related to the scattergram of an analysis result that includes anomaly information of the scattergram such as a fraction anomaly and the like, the comment corresponding to the scattergram included in the analysis result of the display object may be displayed when the identical anomaly information is included in the analysis result of the display object.

Although the above embodiments are described in terms of setting the reading authority for each user group, the present invention is not limited to this arrangement. The reading authority need not be set for each user group inasmuch as the reading authority may also be set for each user. That is, the reading authority may be set so as to permit or prohibit reading of a comment for individual users such as predetermined physicians, and predetermined technologists.

Although the above embodiments are described in terms of displaying a comment when a mouse cursor overlaps a comment icon, the present invention is not limited to this arrangement. The CPU may determine whether a mouse cursor is within a predetermined region which includes the vicinity of the comment icon, and receive the specification of the item corresponding to the region by causing the mouse cursor to enter the region.

Although the above embodiments have been described in terms of displaying a comment corresponding to an item in a pop-up when a comment icon is displayed near the item related to the comment in the analysis result screen and the comment icon has been specified, the present invention is not limited to this arrangement. The comment may also be displayed simultaneously with the start of the display of the analysis result screen without displaying a comment icon. In this case, it is desirable that the comment display can be ended independently of the analysis result screen. Thus, when part of the analysis result is obscured by the comment, the hidden part of the analysis result can be displayed by ending the comment display. The comment may also be displayed so as to not overlap the analysis result.

Although the above embodiments are described in terms of displaying a comment icon near an item relate to a comment in the analysis result screen, the present invention is not limited to this arrangement. A comment may also be displayed in a pop-up by displaying a comment-linked button or text string (text data) without an icon, and selecting the button or text string by clicking the mouse.

Although the above embodiments are described in terms of displaying a comment in a pop-up when a comment icon displayed on the analysis result screen has been specified, the present invention is not limited to this arrangement. When the comment icon has been specified, a window displaying the comment may be displayed separately from the window displaying the analysis result screen rather than displaying the comment in a pop-up.

Although the above embodiments are described in terms of a sample analyzer configured by separately provided measuring unit and information processing unit, the present invention is not limited to this configuration inasmuch as the function of the measuring unit and the function of the information processing unit may be integratedly provided as one unit in a sample analyzer.

Although the above embodiments are described in terms of executing all processes of the analysis program 34a by a single computer 3a in the above embodiments, the present invention is not limited to this configuration inasmuch as a dispersed system in which processes similar to those of the analysis program 34a are dispersed and executed by a plurality of devices (computers) is also possible.

What is claimed is:

1. A sample analyzer comprising:
an analysis result information generator for generating a first analysis result information including a first analysis result of a first sample;
a display;
a display controller for controlling the display;
an input receiver for receiving an input of a first comment to the first analysis result information;
a memory for storing the first comment with the first analysis result information; and
a determiner for determining whether a second analysis result information, which includes a second analysis result of a second sample different from the first sample, meets with a predetermined condition,
wherein the display controller controls the display so as to display an analysis result screen including the first comment and the second analysis result information which has been determined to meet with the predetermined condition.

2. The sample analyzer of claim 1, wherein
the first analysis result information includes a plurality of information classified into a plurality of items related to the first sample;
the first comment corresponds to information of one item of the plurality of items;
the determiner determines whether information of the one item in the second analysis result information meets with the predetermined condition by comparing the information of the one item corresponding to the first comment received by the input receiver with the information of the one item in the second analysis result information; and
the first comment stored in the memory is displayed on the display so as to be associated with the information of the one item in the second analysis result information, when the determiner has determined that the information of the one item in the second analysis result information meets with the predetermined condition.

3. The sample analyzer of claim 2, wherein
the memory stores the analysis result information, and stores comment retrieval information that includes the first comment received by the input receiver and the information of the one item corresponding to the first comment;
the determiner compares the information of the one item corresponding to the first comment included in the comment retrieval information with the information of the one item in the second analysis result information; and
the first comment included in the comment retrieval information is displayed on the display, when the determiner has determined that the information of the one item in the second analysis result information meets with the predetermined condition.

4. The sample analyzer of claim 3, wherein
the input receiver receives specifications of a plurality of items and receives inputs of a plurality of comments corresponding to the plurality of specified items respectively;
the comment retrieval information includes the plurality of comments and information of the plurality of items corresponding to the plurality of comments respectively;
the determiner determines whether each information of the plurality of items in the second analysis result information meets with the predetermined condition by comparing, for each comment included in the comment retrieval information, the information of the plurality of items corresponding to the plurality of comments with the information of the plurality of items in the second analysis result information; and
all comments corresponding to items determined by the determiner to meet the predetermined condition are displayed on the display.

5. The sample analyzer of claim 2, wherein
the plurality of information classified to the plurality of items include a particle distribution diagram representing distribution state relating to characteristic parameter information indicating characteristic of particles in the first sample;
the determiner determines, when the information of the item corresponding to the first comment received by the input receiver is a particle distribution diagram, whether the particle distribution diagram corresponding to the first comment is similar to a particle distribution diagram included in the another second analysis result information; and
the comment is displayed on the display when the determiner has determined that the two particle distribution diagram is similar.

6. The sample analyzer of claim 2, wherein
the plurality of information classified to the plurality of items include patient identification information identifying a patient from whom the first sample has been collected;
the determiner determines, when the information of the item corresponding to the first comment received by the input receiver is patient identification information, whether the patient identification information corresponding to the first comment matches patient identification information included in the another second analysis result information; and
the first comment is displayed on the display when the determiner has determined that the two patient identification information match.

7. The sample analyzer of claim 2, wherein
the plurality of information classified to the plurality of items include physician identification information identifying a physician of a patient from whom the first sample has been collected;
the determiner determines, when the information of the item corresponding to the first comment received by the input receiver is physician identification information, whether the physician identification information corresponding to the first comment matches physician identification information included in the another second analysis result information; and
the first comment is displayed on the display when the determiner has determined that the two physician identification information match.

8. The sample analyzer of claim 1, further comprising:
an observer identification information receiver for receiving input of observer identification information identifying an observer of the second analysis result information before the second analysis result information is displayed on the display;
a comment display determiner for determining whether to permit or prohibit displaying the first comment, based on the observer identification information received by the observer identification information receiver;
wherein the second analysis result information and the first comment are displayed on the display when the comment display determiner has determined to permit displaying the first comment, and the second analysis result information is displayed on the display without the first comment when the comment display determiner has determined to prohibit displaying the first comment.

9. The sample analyzer of claim 1,
wherein the second analysis result information and a specifiable specifying part indicating a presence of a displayable comment are displayed on the display by the display controller, when the determiner has determined that the second analysis result information meets with the predetermined condition;
the sample analyzer further comprises a specification determiner for determining whether the specifying part displayed on the display has been specified;
and wherein the first comment is displayed on a display screen displaying the second analysis result information by the display controller, when the specification determiner has determined that the specifying part has been specified.

10. The sample analyzer of claim 9, wherein
the specifying part is an icon.

11. The analyzer of claim 9, further comprising:
a cancellation determiner for determining whether the specification of the specifying part has been cancelled,
wherein display of the first comment is ended by the display controller, when the cancellation determiner has determined that the specification of the specifying part has been cancelled.

12. A sample analyzer comprising:
a display;
a memory; and
a controller being configured to perform operations, comprising:
generating a first analysis result information including a first analysis result of a first sample;
receiving an input of a first comment to the first analysis result information;
storing the first comment with the first analysis result information in the memory;

determining whether a second analysis result information, which includes a second analysis result of a second sample different from the first sample, meets with a predetermined condition; and controlling the display so as to display an analysis result screen including the first comment and the second analysis result information which has been determined to meet with the predetermined condition.

13. A method for displaying analysis result information of a sample, comprising steps of:
   (a) generating a first analysis result information including a first analysis result of a first sample;
   (b) receiving an input of a first comment to the first analysis result information;
   (c) storing the first comment with the first analysis result information in a memory;
   (d) determining whether a second analysis result information, which includes a second analysis result of a second sample different from the first sample, meets with a predetermined condition; and
   (e) displaying an analysis result screen including the first comment and the second analysis result information which has been determined to meet with the predetermined condition in the step (d).

14. The method of claim 13, wherein
the first analysis result information includes a plurality of information classified into a plurality of items related to the first sample;
the first comment corresponds to information of one item of the plurality of items;
the step (d) comprises a step of determining whether information of the one item in the second analysis result information meets with the predetermined condition by comparing the information of the one item corresponding to the first comment received in the step (b) with the information of the one item in the second analysis result information; and
the step (e) comprises a step of displaying the first comment stored in the memory so as to be associated with the information of the one item in the second analysis result information, when it has been determined that the information of the one item in the second analysis result information meets with the predetermined condition in the step (d).

15. The method of claim 14, wherein
the step (c) comprises a step of storing the first analysis result information in the memory, and a step of storing, in the memory, comment retrieval information that includes the first comment received in the step (b) and the information of the one item corresponding to the first comment;
the step (d) comprises a step of comparing the information of the one item corresponding to the first comment included in the comment retrieval information with the information of the one item in the second analysis result information; and
the step (e) comprises a step of displaying the first comment included in the comment retrieval information, when it has been determined that the information of the one item in the second analysis result information meets with the predetermined condition in the step (d).

16. The method of claim 15, wherein
the step (b) comprises a step of receiving specifications of a plurality of items and receiving inputs of a plurality of comments corresponding to the plurality of specified items respectively;
the comment retrieval information includes the plurality of comments and information of the plurality of items corresponding to the plurality of comments respectively;
the step (d) comprises a step of determining whether each information of the plurality of items in the second analysis result information meets with the predetermined condition by comparing, for each comment included in the comment retrieval information, the information of the plurality of items corresponding to the plurality of comments with the information of the plurality of items in the second analysis result information; and
the step (e) comprises a step of displaying all comments corresponding to items determined in the step (d) to meet the predetermined condition.

17. The method of claim 14, wherein
the plurality of information classified to the plurality of items include a particle distribution diagram representing distribution state relating to characteristic parameter information indicating characteristic of particles in the first sample;
the step (d) comprises a step of determining, when the information of the item corresponding to the first comment received in the step (b) is a particle distribution diagram, whether the particle distribution diagram corresponding to the first comment is similar to a particle distribution diagram included in the second analysis result information; and
the step (e) comprises a step of displaying the first comment when it has been determined that the two particle distribution diagram is similar in the step (d).

18. The method of claim 14, wherein
the plurality of information classified to the plurality of items include patient identification information identifying a patient from whom the first sample has been collected;
the step (d) comprises a step of determining, when the information of the item corresponding to the first comment received in the step (b) is patient identification information, whether the patient identification information corresponding to the first comment matches patient identification information included in the second analysis result information; and
the step (e) comprises a step of displaying the first comment when it has been determined that the two patient identification information match in the step (d).

19. The method of claim 14, wherein
the plurality of information classified to the plurality of items include physician identification information identifying a physician of a patient from whom the first sample has been collected;
the step (d) comprises a step of determining, when the information of the item corresponding to the first comment received in the step (b) is physician identification information, whether the physician identification information corresponding to the first comment matches physician identification information included in the another second analysis result information; and
the step (e) comprises a step of displaying the first comment when it has been determined that the two physician identification information match in the step (d).

20. A non-transitory computer readable medium containing computer instructions stored therein for cause a computer processor to perform predetermined operations comprising:
   (a) generating a first analysis result information including a first analysis result of a first sample;
   (b) receiving an input of a first comment to the first analysis result information;

(c) storing the first comment with the first analysis result information in a memory;
(d) determining whether a second analysis result information, which includes a second analysis result of a second sample different from the first sample, meets with a predetermined condition; and
(e) displaying an analysis result screen including the first comment and the second analysis result information which has been determined to meet with the predetermined condition.

* * * * *